US012678626B2

(12) United States Patent
Dinsmoor et al.

(10) Patent No.: US 12,678,626 B2
(45) Date of Patent: Jul. 14, 2026

(54) DETERMINING ELECTRODE COMBINATIONS FOR SENSING

(71) Applicant: Medtronic, Inc., Minneapolis, MN (US)

(72) Inventors: David A. Dinsmoor, North Oaks, MN (US); Juan G. Hincapie, Maple Grove, MN (US); Leonid M. Litvak, Bet Shemesh (IL)

(73) Assignee: Medtronic, Inc., Minneapolis, MN (US)

( * ) Notice: Subject to any disclaimer, the term of this patent is extended or adjusted under 35 U.S.C. 154(b) by 225 days.

(21) Appl. No.: 18/546,917

(22) PCT Filed: Feb. 21, 2022

(86) PCT No.: PCT/US2022/017157
§ 371 (c)(1),
(2) Date: Aug. 17, 2023

(87) PCT Pub. No.: WO2022/182611
PCT Pub. Date: Sep. 1, 2022

(65) Prior Publication Data
US 2024/0307690 A1 Sep. 19, 2024

Related U.S. Application Data

(60) Provisional application No. 63/153,020, filed on Feb. 24, 2021.

(51) Int. Cl.
*A61N 1/36* (2006.01)
(52) U.S. Cl.
CPC ................................ *A61N 1/36139* (2013.01)
(58) Field of Classification Search
None
See application file for complete search history.

(56) References Cited

U.S. PATENT DOCUMENTS 6,266,558 B1 7/2001 Gozani et al.
8,165,687 B2 4/2012 Cruz et al.
(Continued)

FOREIGN PATENT DOCUMENTS

EP 1972359 A2 9/2008
EP 3024540 A1 6/2016
(Continued)

OTHER PUBLICATIONS

Abbas et al., "Channel interaction in cochlear implant users evaluated using the electrically evoked compound action potential", Audiology and Neurotology, vol. 9, No. 4, S. Karger AG, Basel, Feb. 10, 2004, pp. 203-213.
(Continued)

*Primary Examiner* — Carl H Layno
*Assistant Examiner* — Bryan McAllister Lee
(74) *Attorney, Agent, or Firm* — Shumaker & Sieffert, P.A.

(57) ABSTRACT

Systems, devices, and techniques for analyzing evoked compound action potentials (ECAP)signals to evaluate and select an electrode combination. A method includes controlling, by processing circuitry, deliver of a plurality of stimulation pulses via at least one stimulation electrode combination, receiving, by the processing circuitry, evoked compound action potential (ECAP) signal information representing different ECAP signals evoked from respective stimulation pulses of the plurality of stimulation pulses and obtained from respective different sensing electrode combinations, selecting by the processing circuitry and based on the ECAP signal information, one electrode combination from the different sensing electrode combinations.

20 Claims, 15 Drawing Sheets

(56) References Cited

U.S. PATENT DOCUMENTS

| | | | |
|---|---|---|---|
| 9,381,356 | B2 | 7/2016 | Parker et al. |
| 10,183,168 | B2 | 1/2019 | Baru et al. |
| 11,337,658 | B2 | 5/2022 | Single |
| 2005/0261748 | A1 | 11/2005 | Van Dijk |
| 2010/0249643 | A1 | 9/2010 | Gozani et al. |
| 2011/0245891 | A1 | 10/2011 | Fritsch et al. |
| 2013/0274827 | A1 | 10/2013 | Smoorenburg |
| 2015/0005842 | A1 | 1/2015 | Lee et al. |
| 2015/0032181 | A1 | 1/2015 | Baynham et al. |
| 2016/0157769 | A1 | 6/2016 | Min et al. |
| 2016/0199642 | A1 | 7/2016 | Schwarz et al. |
| 2017/0361101 | A1 | 12/2017 | Single |
| 2019/0099602 | A1* | 4/2019 | Esteller .............. A61N 1/37241 |
| 2019/0175904 | A1 | 6/2019 | Baru et al. |
| 2019/0275331 | A1 | 9/2019 | Zhu |
| 2019/0388692 | A1 | 12/2019 | Dinsmoor et al. |
| 2019/0388695 | A1 | 12/2019 | Dinsmoor et al. |
| 2020/0029914 | A1 | 1/2020 | Single |

FOREIGN PATENT DOCUMENTS

| | | | |
|---|---|---|---|
| EP | 3337555 | A1 | 6/2018 |
| WO | 2004084722 | A1 | 10/2004 |
| WO | 2015013398 | A1 | 1/2015 |
| WO | 2015095665 | A1 | 6/2015 |
| WO | 2016090436 | A1 | 6/2016 |
| WO | 2016161484 | A1 | 10/2016 |
| WO | 2017028906 | A1 | 2/2017 |
| WO | 2017173493 | A1 | 10/2017 |
| WO | 2022126057 | A1 | 6/2022 |

OTHER PUBLICATIONS

Adenis et al., "ECAP growth function to increasing pulse amplitude or pulse duration demonstrates large inter-animal variability that is reflected in auditory cortex of the guinea pig", PLOS ONE, vol. 13, No. 8, Aug. 2, 2018, 24 pp., https://doi.org/10.1371/journal.pone.0201771.

Akin et al., "Results of a multicenter clinical study evaluating a new smart algorithm to measure neural response imaging", Otology & Neurotology, vol. 33, No. 5, Otology & Neurotology, Inc, Jul. 1, 2012, pp. 736-739.

Brown et al., "Electrically evoked whole nerve action potentials: data from human cochlear implant users", The Journal of the Acoustical Society of America, vol. 88, No. 3, Acoustical Society of America, Sep. 1, 1990, pp. 1385-1391.

Brown et al., "Preliminary experience with Neural Response Telemetry in the Nucleus CI24M cochlear implant", The American Journal of Otology, vol. 19, No. 3, The American Journal of Otology, Inc, May 1, 1998, pp. 320-327.

Cedeno et al., "Spinal cord stimulation using differential target multiplexed programming modulates neural cell-specific transcriptomes in an animal model of neuropathic pain", Molecular Pain, vol. 16, Sage, Oct. 13, 2020, 8 pp., doi: 10.1177/1744806920964360.

Chakravarthy et al., "Sensing Evoked Compound Action Potentials from the Spinal Cord: Novel Preclinical and Clinical Considerations for the Pain Management Researcher and Clinician", Journal of Pain Research, vol. 13, Dovepress, Dec. 4, 2020, pp. 3269-3279, doi.org/10.2147/JPR.S289098.

He et al., "Perception threshold and electrode position for spinal cord stimulation", PAIN, vol. 59, No. 1, Elsevier Science B.V., Feb. 23, 1994, pp. 55-63.

Holsheimer et al., "MR Asessment of the Normal Position of the Spinal Cord in the Spinal Cord", American Society of Neuroradiology, vol. 15, No. 5, May 1994, pp. 951-959.

International Preliminary Report on Patentability from International Application No. PCT/US2022/017157 dated Sep. 7, 2023, 7 pp.

International Search Report and Written Opinion of International Application No. PCT/US2022/017157, dated May 27, 2022, 10 pp.

Laird-Wah, "Improving Spinal Cord Stimulation", Graduate School of Biomedical Engineering, University of New South Wales, Aug. 2015, 273 pp.

Lempka et al., "Patient-Specific Analysis of Neural Activation During Spinal Cord Stimulation for Pain", Neuromodulation: Technology at the Neural Interface, vol. 23, PubMed, Aug. 28, 2019, pp. 572-581, doi: 10.1111/ner.13037.

Mekhail et al., "Evoked compound action potential recording to further understand effect of titrating medication with spinal cord stimulation—case study", EFIC congress, Sep. 3, 2019, 1 pp.

Mekhail et al., "Long-term safety and efficacy of closed-loop spinal cord stimulation to treat chronic back and leg pain (Evoke): a double-blind, randomised, controlled trial. Lancet Neurol", The Lancet Neurology, vol. 19, No. 2, Elsevier Ltd, Feb. 1, 2020, pp. 123-134.

Melzack et al., "Pain Mechanisms: A New Theory", Science, vol. 150, No. 3699, Nov. 19, 1965, pp. 971-979, doi: 10.1126/science.150.3699.971.

Miller et al., "An improved method of reducing stimulus artifact in the electrically evoked whole-nerve potential", Ear and hearing, vol. 21, No. 4, Lippincott Williams & Wilkins, Aug. 1, 2000, pp. 280-290.

Miller et al., "Electrically evoked compound action potentials of guinea pig and cat: responses to monopolar, monophasic stimulation. Hear", Hearing research, vol. 119, No. 1-2, Elsevier, May 1, 1998, pp. 142-154.

Morsnowski et al., "Measuring the refractoriness of the electrically stimulated auditory nerve", Audiology and Neurotology, vol. 11, No. 6, S. Karger AG, Basel, Sep. 27, 2006, pp. 389-402.

Nehme et al., "Measures of the electrically evoked compound action potential threshold and slope in HiRes 90KTM users", Cochlear implants international, vol. 15, No. 1, W.S. Maney & Son Ltd, Jan. 6, 2014, pp. 53-60.

Parker et al., "Compound action potentials recorded in the human spinal cord during neurostimulation for pain relief", vol. 153, No. 3, Elsevier B.V., Nov. 21, 2011, pp. 593-601.

Parker et al., "Evoked compound action potentials reveal spinal cord dorsal col. neuroanatomy", Neuromodulation: Technology at the Neural Interface, International Neuromodulation Society, Mar. 19, 2019, pp. 82-95.

Ren et al., "Neuron-glia crosstalk gets serious: role in pain hypersensitivity", Current Opinion in Anesthesiology, vol. 21, No. 5, Oct. 2008, pp. 570-579, doi: 10.1097/ACO.0b013e32830edbdf.

Russo et al., "Effective Relief of Pain and Associated Symptoms With Closed-Loop Spinal Cord Stimulation System: Preliminary Results of the Avalon Study", Neuromodulation: Technology at the Neural Interface, vol. 21, No. 1, International Neuromodulation Society, Jul. 17, 2017, pp. 38-47.

Sankarasubramanian et al., "Triple Leads Programmed to Perform as Longitudinal Guarded Cathodes in Spinal Cord Stimulation: A Modeling Study", Neuromodulation: Technology at the Neural Interface, vol. 14, No. 5, Sep. 2011, pp. 401-411, doi: 10.1111/j.1525-1403.2011.00383.x.

Shealy et al., "Electrical Inhibition of Pain by Stimulation of the Dorsal cols. Preliminary Clinical Report", Anesthesia & Analgesia, vol. 46, No. 4, International Anesthesia Research Society, Jul. 1967, pp. 489-491.

Single et al., "Cause of Pulse Artefacts Inherent to the Electrodes of Neuromodulation Implants", IEEE Transactions on Neural Systems and Rehabilitation Engineering, vol. 26, No. 10, EMB, Oct. 2018, pp. 2078-2083, DOI: 10.1109/TNSRE.2018.2870169.

Stanslaski et al., "Design and validation of a fully implantable, chronic, closed-loop neuromodulation device with concurrent sensing and stimulation", IEEE Transactions on Neural Systems and Rehabilitation Engineering, vol. 20, No. 4, IEEE, Jan. 23, 2012, pp. 410-421.

U.S. Appl. No. 18/270,810, filed Jan. 7, 2022, naming inventors Litvak et al.

Van De Honert et al., "Characterization of the electrically evoked auditory brainstem response (EABR) in cats and humans", Hearing research, Elsevier Science Publishers B.V., Oct. 31, 1985, pp. 109-126.

(56) References Cited

OTHER PUBLICATIONS

Wu et al., "Spinal Cord Stimulation", Clinicalgate, Feb. 27, 2015, 15 pp., URL: https://clinicalgate.com/spinal-cord-stimulation-6/.
Office Action from U.S. Appl. No. 18/270,810 dated Jul. 1, 2025, 10 pp.
Final Office Action from U.S. Appl. No. 18/270,810 dated Oct. 27, 2025, 11 pp.
Response to Office Action dated Jul. 1, 2025 from U.S. Appl. No. 18/270,810, filed Oct. 1, 2025, 11 pp.
Advisory Action from U.S. Appl. No. 18/270,810 dated Jan. 2, 2026, 2 pp.
Response to Final Office Action dated Oct. 27, 2025 from U.S. Appl. No. 18/270,810, filed Dec. 22, 2025, 12 pp.
Pre-Appeal Brief Request for Review from U.S. Appl. No. 18/270,810, filed Jan. 27, 2026, 4 pp.
Corrected Notice of Allowance from U.S. Appl. No. 18/270,810 dated Apr. 24, 2026, 5 pp.
Notice of Allowance from U.S. Appl. No. 18/270,810 dated Apr. 10, 2026, 8 pp.

* cited by examiner

290

902   DELIVER PLURALITY OF STIMULATION PULSES TO MULTIPLE ELECTRODE CONFIGURATIONS

904   SENSE ECAP SIGNAL RESULTING FROM STIMULATION PULSES

906   DETERMINE ECAP SIGNAL CHARACTERISTIC VALUES

908   DETERMINE ELECTRODE CONFIGURATION BASED ON ECAP SIGNAL CHARACTERISTIC VALUES

DETERMINING ELECTRODE COMBINATIONS FOR SENSING

This application is a national stage entry of International Patent Application No. PCT/US2022/017157, filed Feb. 21, 2022, which claims priority to and the benefit of U.S. Provisional Patent Application Ser. No. 63/153,020, entitled "DETERMINING ELECTRODE COMBINATIONS FOR SENSING" and filed on Feb. 24, 2021, the entire contents of application nos. PCT/US2022/017157 and 63/153,020 are incorporated by reference herein.

TECHNICAL FIELD

This disclosure generally relates to medical devices, and more specifically, to determining electrode combinations for sensing electrical signals.

BACKGROUND

Medical devices may be external or implanted and may be used to deliver electrical stimulation therapy to patients via various tissue sites to treat a variety of symptoms or conditions such as chronic pain, tremor, Parkinson's disease, epilepsy, urinary or fecal incontinence, sexual dysfunction, obesity, or gastroparesis. A medical device may deliver electrical stimulation therapy via one or more leads that include electrodes located proximate to target locations associated with the brain, the spinal cord, pelvic nerves, peripheral nerves, or the gastrointestinal tract of a patient. Stimulation proximate the spinal cord, proximate the sacral nerve, within the brain, and proximate peripheral nerves are often referred to as spinal cord stimulation (SCS), sacral neuromodulation (SNM), deep brain stimulation (DBS), and peripheral nerve stimulation (PNS), respectively.

Electrical stimulation may be delivered to a patient by the medical device in a train of electrical pulses, and parameters of the electrical pulses may include a frequency, an amplitude, a pulse width, and a pulse shape. An evoked compound action potential (ECAP) is synchronous firing of a population of neurons which occurs in response to the application of a stimulus including, in some cases, an electrical stimulus by a medical device. The ECAP may be detectable as being a separate event from the stimulus itself, and the ECAP may reveal characteristics of the effect of the stimulus on the nerve fibers.

SUMMARY

In general, systems, devices, and techniques are described for systems, devices, and techniques for analyzing evoked compound action potentials (ECAP) signals to evaluate and select an electrode combination. For example, a system may control delivery of a plurality of stimulation pulses to at least one stimulation electrode combination. The system may detect and then receive ECAP signal information obtained from different sensing electrode combinations. Based on the ECAP signal information, the system may select one electrode combination from the multiple different sensing electrode combinations. In other words, the system may be configured to analyze ECAP signals to evaluate and select an electrode combination for sensing ECAP signals from the patient that the system may then use for adjusting stimulation therapy.

In one or more examples, a method includes controlling, by processing circuitry, delivery of a plurality of stimulation pulses via at least one stimulation electrode combination, receiving, by the processing circuitry, evoked compound action potential (ECAP) signal information representing different ECAP signals evoked from respective stimulation pulses of the plurality of stimulation pulses and obtained from respective different sensing electrode combinations, selecting, by the processing circuitry and based on the ECAP signal information, one electrode combination from the different sensing electrode combinations.

In some examples, a device includes processing circuitry configured to control, by the processing circuitry, delivery of a plurality of stimulation pulses via at least one stimulation electrode combination, receive, by the processing circuitry, evoked compound action potential (ECAP) signal information representing different ECAP signals evoked from respective stimulation pulses of the plurality of stimulation pulses and obtained from respective different sensing electrode combinations, and select, by the processing circuitry and based on the ECAP signal information, one electrode combination from the different sensing electrode combinations.

In some examples, a computer-readable storage medium includes instructions that, when executed, cause processing circuitry to control delivery of a plurality of stimulation pulses via at least one stimulation electrode combination; receive evoked compound action potential (ECAP) signal information representing different ECAP signals evoked from respective stimulation pulses of the plurality of stimulation pulses and obtained from respective different sensing electrode combinations and select, based on the ECAP signal information, one electrode combination from the different sensing electrode combinations.

The summary is intended to provide an overview of the subject matter described in this disclosure. It is not intended to provide an exclusive or exhaustive explanation of the systems, device, and methods described in detail within the accompanying drawings and description below. Further details of one or more examples of this disclosure are set forth in the accompanying drawings and in the description below. Other features, objects, and advantages will be apparent from the description and drawings, and from the claims.

DETAILED DESCRIPTION

Figure 1:
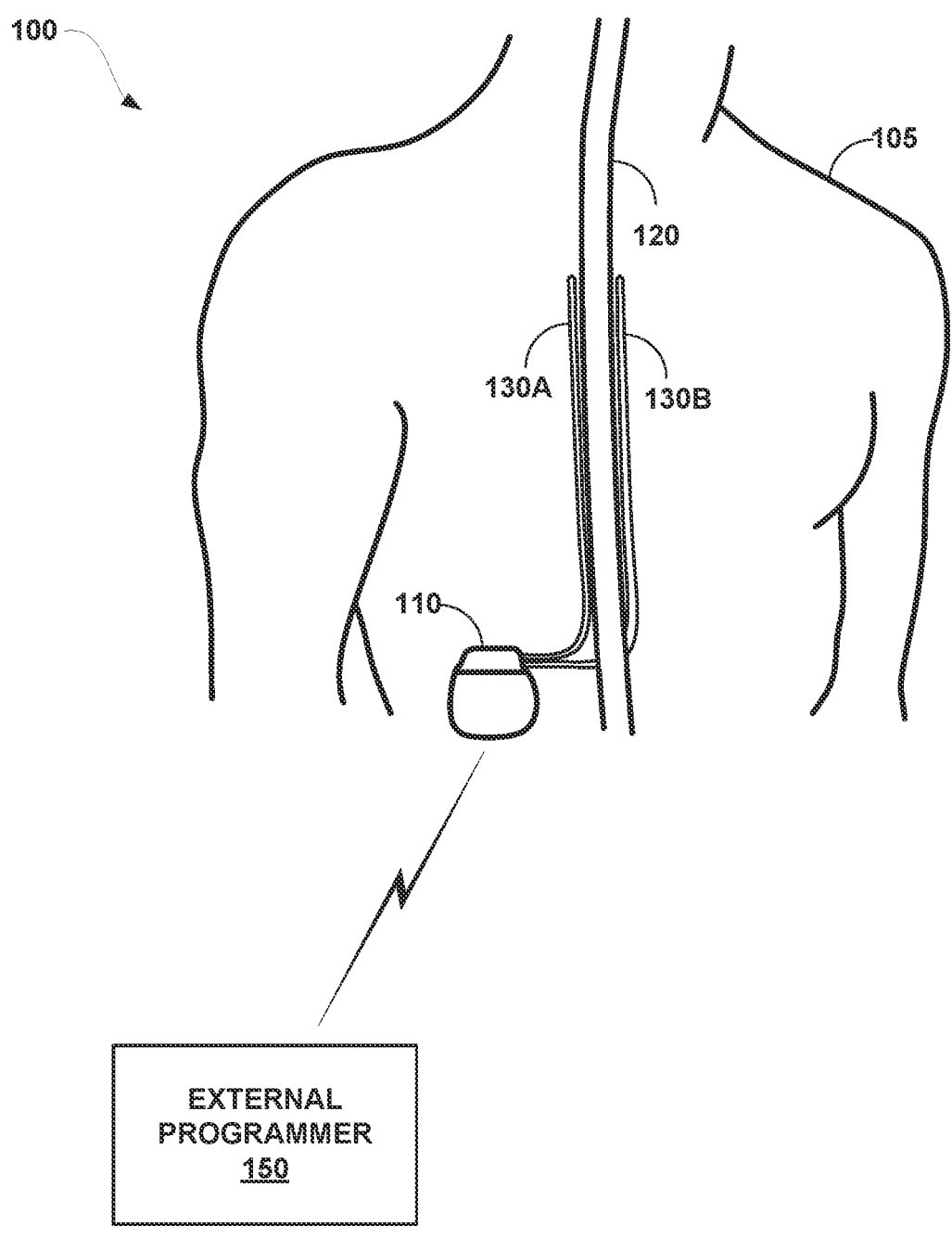
FIG. 1 is a conceptual diagram illustrating an example system that includes an implantable medical device (IMD) configured to deliver spinal cord stimulation (SCS) therapy and an external programmer, in accordance with one or more techniques of this disclosure.

The disclosure describes examples of medical devices, systems, and techniques for analyzing evoked compound action potentials (ECAP) signals evaluation and selection of electrode combinations based on ECAP signals. Electrical stimulation therapy is typically delivered to a target tissue (e.g., nerves of the spinal cord or muscle) of a patient via two or more electrodes. Parameters of the electrical stimulation therapy (e.g., electrode combination, voltage or current amplitude, pulse width, pulse frequency, etc.) are selected by a clinician and/or the patient to provide relief from various symptoms, such as pain, nervous system disorders, muscle disorders, etc. Various thresholds, such as a perception threshold and/or discomfort threshold may be determined for the patient and used to select and/or recommend electrode combinations of the stimulation therapy.

ECAPs are a measure of neural recruitment because each ECAP signal represents the superposition of electrical potentials generated from a population of axons firing in response to an electrical stimulus (e.g., a stimulation pulse). Changes in a characteristic (e.g., an amplitude of a portion of the signal or area under the curve of the signal) of an ECAP signals occur as a function of how many axons have been activated by the delivered stimulation pulse. For a given set of parameter values that define the stimulation pulse and a given distance between the electrodes and target nerve, the detected ECAP signal may have a certain characteristic value (e.g., amplitude).

In some examples, effective stimulation therapy may rely on a certain level of neural recruitment at a target nerve. This effective stimulation therapy may provide relief from one or more conditions (e.g., patient perceived pain) without an unacceptable level of side effects (e.g., overwhelming perception of stimulation).

Although the system may adjust one or more stimulation parameters according to the one or more characteristics of the sensed ECAP signal, for example, to compensate for the change in distance between electrodes and nerves, the precision of such adjustments is dependent on accurately determining the characteristics of the ECAP signal. For example, noise such as stimulation artifacts and/or linear or exponential background noise may interfere with accurate determinations of the magnitude of one or more peaks within the ECAP signal. Stimulation artifacts typically have amplitudes many times that of the ECAP signal and can at least partially overlap with the ECAPs from nerves. Inaccurate ECAP characterization can reduce the effectiveness of using ECAP characteristic values for automatically adjusting stimulation parameters and result in less efficacious therapy for the patient. Moreover, manually identifying patient thresholds, such as a perception threshold, can be time consuming and rely on subjective feedback from the patient. Therefore, clinicians may be pressed for time when setting up stimulation, perception thresholds may be inaccurate, and patients may need to return to the clinic in order to update the stimulator programming for example. These issues may reduce the likelihood that the patient receives efficacious therapy that could be provided.

In general, it is preferred to maximize the electrophysiologic component of the ECAP while minimizing the stimulation artifact. These considerations are particularly important for SCS systems where there are many electrodes on a tight pitch from which to choose. For leads with fewer electrodes, such as conventional 8-contact (1×8) percutaneous leads, there are relatively few options available for electrode combination. For higher density leads, such as a 5-6-5 lead or paddle leads, far more sensing combinations are available that may include traverse combinations, e.g., sensing combinations where the sensing vector is not parallel to the stimulation vector from the stimulation electrodes (traverse combinations may be electrodes that form a line that is not parallel to or orthogonal to the line formed by the stimulation electrodes). The ECAP characteristic values can be used by the system and/or clinician in order to select a sensing electrode combination that may provide improved sensing abilities compared to other possible sensing electrode combinations.

As described herein, systems, devices, and techniques are described for analyzing an ECAP signal sensed from the patient in order to determine one or more characteristic values of the ECAP signal and to use the one or more characteristic values of the ECAP signal, which is used to determine a preferred electrode combination for sensing ECAP signals. In one example, the system may attempt to reduce the impact of artifacts through selection of sensing configurations.

In some examples, the ECAPs detected by an IMD may be ECAPs elicited by stimulation pulses intended to contribute to therapy of a patient or separate pulses (e.g., control pulses) configured to elicit ECAPs that are detectable by the IMD. Nerve impulses detectable as the ECAP signal travel quickly along the nerve fiber after the delivered stimulation pulse first depolarizes the nerve. If the stimulation pulse delivered by first electrodes has a pulse width that is too long, different electrodes configured to sense the ECAP will sense the stimulation pulse itself as an artifact (e.g., detection of delivered charge itself as opposed to detection of a physiological response to the delivered stimulus) that obscures the lower amplitude ECAP signal. However, the ECAP signal loses fidelity as the electrical potentials propagate from the electrical stimulus because different nerve fibers propagate electrical potentials at different speeds and fibers in spine contributing to the ECAP are pruned off. Therefore, sensing the ECAP at a far distance from the stimulating electrodes may avoid the artifact caused by a stimulation pulse with a long pulse width, but the ECAP signal may be too small or lose fidelity needed to detect changes to the ECAP signal that occur when the electrode to target tissue distance changes. In other words, the system may not be able to identify, at any distance from the stimulation electrodes, ECAPs from stimulation pulses configured to provide a therapy to the patient.

FIG. 1 is a conceptual diagram illustrating an example system 100 that includes an implantable medical device (IMD) 110 configured to deliver spinal cord stimulation (SCS) therapy and an external programmer 150, in accordance with one or more techniques of this disclosure. Although the techniques described in this disclosure are generally applicable to a variety of medical devices including external devices and IMDs, application of such techniques to IMDs and, more particularly, implantable electrical stimulators (e.g., neurostimulators) will be described for purposes of illustration. More particularly, the disclosure will refer to an implantable SCS system for purposes of illustration, but without limitation as to other types of medical devices or other therapeutic applications of medical devices.

As shown in FIG. 1, system 100 includes an IMD 110, leads 130A and 130B, and external programmer 150 shown in conjunction with a patient 105, who is ordinarily a human patient. In the example of FIG. 1, IMD 110 is an implantable electrical stimulator that is configured to generate and deliver electrical stimulation therapy to patient 105 via one or more electrodes of electrodes of leads 130A and/or 130B (collectively "leads 130"), e.g., for relief of chronic pain or other symptoms. In other examples, IMD 110 may be coupled to a single lead carrying multiple electrodes or more than two leads each carrying multiple electrodes. In some examples, the stimulation signals, or pulses, may be configured to elicit detectable ECAP signals that IMD 110 may use to determine the posture state occupied by patient 105 and/or determine how to adjust one or more parameters that define stimulation therapy. IMD 110 may be a chronic electrical stimulator that remains implanted within patient 105 for weeks, months, or even years. In other examples, IMD 110 may be a temporary, or trial, stimulator used to screen or evaluate the efficacy of electrical stimulation for chronic therapy. In one example, IMD 110 is implanted within patient 105, while in another example, IMD 110 is an external device coupled to percutaneously implanted leads. In some examples, IMD 110 uses one or more leads, while in other examples, IMD 110 is leadless.

IMD 110 may be constructed of any polymer, metal, or composite material sufficient to house the components of IMD 110 (e.g., components illustrated in FIG. 2A) within patient 105. In this example, IMD 110 may be constructed with a biocompatible housing, such as titanium or stainless steel, or a polymeric material such as silicone, polyurethane, or a liquid crystal polymer, and surgically implanted at a site in patient 105 near the pelvis, abdomen, or buttocks. In other examples, IMD 110 may be implanted within other suitable sites within patient 105, which may depend, for example, on the target site within patient 105 for the delivery of electrical stimulation therapy. The outer housing of IMD 110 may be configured to provide a hermetic seal for components, such as a rechargeable or non-rechargeable power source. In addition, in some examples, the outer housing of IMD 110 is selected from a material that facilitates receiving energy to charge the rechargeable power source.

Electrical stimulation energy, which may be constant current or constant voltage-based pulses, for example, is delivered from IMD 110 to one or more target tissue sites of patient 105 via one or more electrodes (not shown) of implantable leads 130. In the example of FIG. 1, leads 130 carry electrodes that are placed adjacent to the target tissue of spinal cord 120. One or more of the electrodes may be disposed at a distal tip of a lead 130 and/or at other positions at intermediate points along the lead. Leads 130 may be implanted and coupled to IMD 110. The electrodes may transfer electrical stimulation generated by an electrical stimulation generator in IMD 110 to tissue of patient 105. Although leads 130 may each be a single lead, lead 130 may include a lead extension or other segments that may aid in implantation or positioning of lead 130. In some other examples. IMD 110 may be a leadless stimulator with one or more arrays of electrodes arranged on a housing of the stimulator rather than leads that extend from the housing. In addition, in some other examples, system 100 may include one lead or more than two leads, each coupled to IMD 110 and directed to similar or different target tissue sites.

The electrodes of leads 130 may be electrode pads on a paddle lead, such as a 5-6-5 lead, circular (e.g., ring) electrodes surrounding the body of the lead, conformable electrodes, cuff electrodes, segmented electrodes (e.g., electrodes disposed at different circumferential positions around the lead instead of a continuous ring electrode), any combination thereof (e.g., ring electrodes and segmented electrodes) or any other type of electrodes capable of forming unipolar, bipolar or multipolar electrode combinations for therapy. Ring electrodes arranged at different axial positions at the distal ends of lead 130 will be described for purposes of illustration.

The deployment of electrodes via leads 130 is described for purposes of illustration, but arrays of electrodes may be deployed in different ways. For example, a housing associated with a leadless stimulator may carry arrays of electrodes, e.g., rows and/or columns (or other patterns), to which shifting operations may be applied. Such electrodes may be arranged as surface electrodes, ring electrodes, or protrusions. As a further alternative, electrode arrays may be formed by rows and/or columns of electrodes on one or more paddle leads. In some examples, electrode arrays include electrode segments, which are arranged at respective positions around a periphery of a lead, e.g., arranged in the form of one or more segmented rings around a circumference of a cylindrical lead. In other examples, one or more of leads 130 are linear leads having eight ring electrodes along the axial length of the lead. In another example, the electrodes are segmented rings arranged in a linear fashion along the axial length of the lead and at the periphery of the lead.

The stimulation parameter set of a therapy stimulation program that defines the stimulation pulses of electrical stimulation therapy by IMD 110 through the electrodes of leads 130 may include information identifying which electrodes have been selected for delivery of stimulation according to a stimulation program, the polarities of the selected electrodes, i.e., the electrode combination for the program, voltage or current amplitude, pulse frequency, pulse width, pulse shape of stimulation delivered by the electrodes. These stimulation parameters values that make up the stimulation parameter set that defines pulses may be predetermined parameter values defined by a user and/or automatically determined by system 100 based on one or more factors or user input.

Although FIG. 1 is directed to SCS therapy, e.g., used to treat pain, in other examples system 100 may be configured to treat any other condition that may benefit from electrical stimulation therapy. For example, system 100 may be used to treat tremor, Parkinson's disease, epilepsy, a pelvic floor disorder (e.g., urinary incontinence or other bladder dysfunction, fecal incontinence, pelvic pain, bowel dysfunction, or sexual dysfunction), obesity, gastroparesis, or psychiatric disorders (e.g., depression, mania, obsessive compulsive disorder, anxiety disorders, and the like). In this manner, system 100 may be configured to provide therapy taking the form of deep brain stimulation (DBS), peripheral nerve stimulation (PNS), peripheral nerve field stimulation (PNFS), cortical stimulation (CS), pelvic floor stimulation, gastrointestinal stimulation, or any other stimulation therapy capable of treating a condition of patient 105.

In some examples, lead 130 includes one or more sensors configured to allow IMD 110 to monitor one or more parameters of patient 105, such as patient activity, pressure, temperature, or other characteristics. The one or more sensors may be provided in addition to, or in place of, therapy delivery by lead 130.

IMD 110 is configured to deliver electrical stimulation therapy to patient 105 via selected combinations of electrodes carried by one or both of leads 130, alone or in combination with an electrode carried by or defined by an outer housing of IMD 110. The target tissue for the electrical stimulation therapy may be any tissue affected by electrical stimulation, which may be in the form of electrical stimulation pulses or continuous waveforms. In some examples, the target tissue includes nerves, smooth muscle, or skeletal muscle. In the example illustrated by FIG. 1, the target tissue is tissue proximate spinal cord 120, such as within an intrathecal space or epidural space of spinal cord 120, or, in some examples, adjacent nerves that branch off spinal cord 120. Leads 130 may be introduced into spinal cord 120 in via any suitable region, such as the thoracic, cervical, or lumbar regions. Stimulation of spinal cord 120 may, for example, prevent pain signals from traveling through spinal cord 120 and to the brain of patient 105. Patient 105 may perceive the interruption of pain signals as a reduction in pain and, therefore, efficacious therapy results. In other examples, stimulation of spinal cord 120 may produce paresthesia which may be reduce the perception of pain by patient 105, and thus, provide efficacious therapy results.

IMD 110 is configured to generate and deliver electrical stimulation therapy to a target stimulation site within patient 105 via the electrodes of leads 130 to patient 105 according to one or more therapy stimulation programs. A therapy stimulation program defines values for one or more parameters (e.g., a parameter set) that define an aspect of the therapy delivered by IMD 110 according to that program. For example, a therapy stimulation program that controls delivery of stimulation by IMD 110 in the form of pulses may define values for voltage or current pulse amplitude, pulse width, pulse rate (e.g., pulse frequency), electrode combination, pulse shape, etc. for stimulation pulses delivered by IMD 110 according to that program.

Furthermore, IMD 110 may be configured to deliver stimulation to patient 105 via a combination of electrodes of leads 130, alone or in combination with an electrode carried by or defined by an outer housing of IMD 110 in order to detect ECAP signals. The tissue targeted by the stimulation may be the same or similar tissue targeted by the electrical stimulation therapy, but IMD 110 may deliver stimulation pulses for ECAP signal detection via the same, at least some of the same, or different electrodes.

IMD 110 can deliver stimulation to a target stimulation site within patient 105 via the electrodes of leads 130 according to one or more ECAP stimulation programs to develop a growth curve of the ECAP. The one or more ECAP stimulation programs may be stored in a storage device of IMD 110. Each ECAP program of the one or more ECAP stimulation programs includes values for one or more parameters that define an aspect of the stimulation delivered by IMD 110 according to that program, such as current or voltage amplitude, pulse width, pulse frequency, electrode combination. In some examples, the ECAP stimulation program may also define the number of pules and parameter values for each pulse of multiple pulses within a pulse sweep configured to obtain a plurality of ECAP signals for respective pulses in order to obtain the growth curve that IMD 110 may use to determine an estimated neural threshold of the patient. In some examples, IMD 110 delivers stimulation to patient 105 according to multiple ECAP stimulation programs. Although these functions are described with respect to IMD 110, other devices, such as external programmer 150, may perform these functions such as determining the estimated neural threshold based on the growth curve of ECAP characteristic values.

A user, such as a clinician or patient 105, may interact with a user interface of an external programmer 150 to program IMD 110. Programming of IMD 110 may refer generally to the generation and transfer of commands, programs, or other information to control the operation of IMD 110. In this manner, IMD 110 may receive the transferred commands and programs from external programmer 150 to control stimulation, such as electrical stimulation therapy to develop the growth curve. For example, external programmer 150 may transmit therapy stimulation programs, ECAP stimulation programs, stimulation parameter adjustments, therapy stimulation program selections, ECAP program selections, user input, or other information to control the operation of IMD 110, e.g., by wireless telemetry or wired connection.

In some cases, external programmer 150 may be characterized as a physician or clinician programmer if it is primarily intended for use by a physician or clinician. In other cases, external programmer 150 may be characterized as a patient programmer if it is primarily intended for use by a patient. A patient programmer may be generally accessible to patient 105 and, in many cases, may be a portable device that may accompany patient 105 throughout the patient's daily routine. For example, a patient programmer may receive input from patient 105 when the patient wishes to terminate or change electrical stimulation therapy, when a patient perceives stimulation being delivered or when a patient terminates due to comfort level. In general, a physician or clinician programmer may support selection and generation of programs by a clinician for use by IMD 110, whereas a patient programmer may support adjustment and selection of such programs by a patient during ordinary use. In other examples, external programmer 150 may include, or be part of, an external charging device that recharges a power source of IMD 110. In this manner, a user may program and charge IMD 110 using one device, or multiple devices.

As described herein, information may be transmitted between external programmer 150 and IMD 110. Therefore, IMD 110 and external programmer 150 may communicate via wireless communication using any techniques known in the art. Examples of communication techniques may include, for example, radiofrequency (RF) telemetry and inductive coupling, but other techniques are also contemplated. In some examples, external programmer 150 includes a communication head that may be placed proximate to the patient's body near the IMD 110 implant site to improve the quality or security of communication between IMD 110 and external programmer 150. Communication between external programmer 150 and IMD 110 may occur during power transmission or separate from power transmission.

In some examples, IMD 110, in response to commands from external programmer 150, delivers electrical stimulation therapy according to a plurality of therapy stimulation programs to a target tissue site of the spinal cord 120 of patient 105 via electrodes (not depicted) on leads 130. In some examples, IMD 110 modifies therapy stimulation programs as therapy needs of patient 105 evolve over time. For example, the modification of the therapy stimulation programs may cause the adjustment of at least one parameter of the plurality of therapy pulses. When patient 105 receives the same therapy for an extended period, the efficacy of the therapy may be reduced. In some cases, parameters of the plurality of therapy pulses may be automatically updated. In some examples, IMD 110 may detect ECAP signals from pulses delivered for the purpose of providing therapy to the patient.

In some examples, efficacy of electrical stimulation therapy may be indicated by one or more characteristics of an action potential that is evoked by a stimulation pulse delivered by IMD 110, for example by determining an estimated neural response using the characteristic value of the ECAP signal. Electrical stimulation therapy delivery by leads 130 of IMD 110 may cause neurons within the target tissue to evoke a compound action potential that travels up and down the target tissue, eventually arriving at sensing electrodes of IMD 110. Furthermore, stimulation pulses may also elicit at least one ECAP signal, and ECAPs responsive to stimulation may also be a surrogate for the effectiveness of the therapy and/or the intensity perceived by the patient. The amount of action potentials (e.g., number of neurons propagating action potential signals) that are evoked may be based on the various parameters of electrical stimulation pulses such as amplitude, pulse width, frequency, pulse shape (e.g., slew rate at the beginning and/or end of the pulse), etc. The slew rate may define the rate of change of the voltage and/or current amplitude of the pulse at the beginning and/or end of each pulse or each phase within the pulse. For example, a very high slew rate indicates a steep or even near vertical edge of the pulse, and a low slew rate indicates a longer ramp up (or ramp down) in the amplitude of the pulse. In some examples, these parameters contribute to an intensity of the electrical stimulation. In addition, a characteristic of the ECAP signal (e.g., an amplitude) may change based on the distance between the stimulation electrodes and the nerves subject to the electrical field produced by the delivered control stimulation pulses.

During delivery of control stimulation pulses defined by one or more ECAP test stimulation programs, IMD 110, via two or more electrodes interposed on leads 130, senses electrical potentials of tissue of the spinal cord 120 of patient 105 to measure the electrical activity of the tissue. IMD 110 senses ECAPs from the target tissue of patient 105, e.g., with electrodes on one or more leads 130 and associated sense circuitry. In some examples, IMD 110 receives a signal indicative of the ECAP from one or more sensors, e.g., one or more electrodes and circuitry, internal or external to patient 105. Such an example signal may include a signal indicating an ECAP of the tissue of patient 105.

In the example of FIG. 1, IMD 110 is described as performing a plurality of processing and computing functions. However, external programmer 150 instead may perform one, several, or all of these functions. In this alternative example, IMD 110 functions to relay sensed signals to external programmer 150 for analysis, and external programmer 150 transmits instructions to IMD 110 to adjust the one or more parameters defining the electrical stimulation therapy based on analysis of the sensed signals. For example, IMD 110 may relay the sensed signal indicative of an ECAP to external programmer 150. External programmer 150 may compare the parameter value of the ECAP to the target ECAP characteristic value relative to an estimated neural response, and in response to the comparison, external programmer 150 may instruct IMD 110 to adjust one or more stimulation parameter that defines the electrical stimulation pulses delivered to patient 105.

In the example techniques described in this disclosure, the stimulation parameters and the target ECAP characteristic may be initially set at the clinic but may be set and/or adjusted at home by patient 105. For example, the target ECAP characteristics may be changed to match, be a fraction of, or a multiplier of, a stimulation threshold. In some examples, target ECAP characteristics may be specific to respective different posture states of the patient. Once the target ECAP characteristic values are set, the example techniques allow for automatic adjustment of parameter values that define stimulation pulses to maintain consistent volume of neural activation and consistent perception of therapy for the patient. The ability to change the stimulation parameter values may also allow the therapy to have long term efficacy, with the ability to keep the intensity of the stimulation (e.g., as indicated by the ECAP) consistent by comparing the measured ECAP values to the target ECAP characteristic value. In addition, or alternatively, to maintaining stimulation intensity, IMD 110 may monitor the characteristic values of the ECAP signals to limit one or more parameter values that define stimulation pulses. IMD 110 may perform these changes without intervention by a physician or patient 105.

In some examples, the system changes the target ECAP characteristic value over a period of time, such as according to a change to a stimulation threshold (e.g., a perception threshold or detection threshold). The system may be programmed to change the target ECAP characteristic in order to adjust the intensity of stimulation pulses to provide varying sensations to the patient (e.g., increase or decrease the volume of neural activation). Although the system may change the target ECAP characteristic value, received ECAP signals may still be used by the system to adjust one or more parameter values of the stimulation pulse in order to meet the target ECAP characteristic value.

One or more devices within system 100, such as IMD 110 and/or external programmer 150, may perform various functions as described herein. For example, IMD 110 may include stimulation circuitry configured to deliver electrical stimulation, sensing circuitry configured to sense a plurality ECAP signals, and processing circuitry. The processing circuitry may be configured to control the stimulation circuitry to deliver a plurality of electrical stimulation pulses to different electrode combinations and control the sensing circuitry to detect, after delivery of each electrical stimulation pulse of the plurality of electrical stimulation pulses, a respective ECAP signal of the plurality of ECAP signals, and to determine ECAP characteristic values for each of the ECAP signals. The processing circuitry of IMD 110 may then determine, based on the plurality of ECAP characteristic values, an electrode combination that maximizes neural activation and/or minimizes a stimulation artifact.

In some examples, IMD 110 may include the stimulation circuitry, the sensing circuitry, and the processing circuitry. However, in other examples, one or more additional devices may be part of the system that performs the functions described herein. For example, IMD 110 may include the stimulation circuitry and the sensing circuitry, but external programmer 150 or other external device may include the processing circuitry that at least determines the estimated neural threshold of the patient. IMD 110 may transmit the sensed ECAP signals, or data representing the ECAP signal, to external programmer 150, for example. Therefore, the processes described herein may be performed by multiple devices in a distributed system. In some examples, system 100 may include one or more electrodes that deliver and/or sense electrical signals. Such electrodes may be configured to sense the ECAP signals. In some examples, the same electrodes may be configured to sense signals representative of transient movements of the patient. In other examples, other sensors, such as accelerometers, gyroscopes, or other movement sensors may be configured to sense movement of the patient that indicates the patient may have transitioned to a different posture state.

As described herein, the processing circuitry of IMD 110 may be configured to determine characteristic values for each the plurality of ECAP signals detected after each of the plurality of electrical stimulation pulses. A plurality of stimulation pulses is delivered, where each stimulation pulse may be defined by a different respective value of stimulation parameter, such as an electrode combination. In one or more examples the characteristic value for each ECAP signal is a representation of the ECAP signal according to some metric, and is determined, by the IMD, for example by removing an artifact from the ECAP signal. These characteristic values may thus be used as a metric derived from the ECAP signal the represents the relative nerve fiber activation caused by the delivered stimulation pulse, such as neural activation. In one or more examples, the artifact may be used as the characteristic value, or as a portion of the characteristic value. In this manner, each ECAP signal of the plurality of ECAP signals will be associated with a respective characteristic value of the characteristic values.

In one example, system 100 (which may be or include IMD 110 and/or external programmer 150 or off-site or networked computing systems) may include a stimulation generator configured to deliver a stimulation pulse to patient 105 and sensing circuitry configured to sense an ECAP signal evoked from the stimulation pulse. System 100 may also include processing circuitry configured to determine ECAP characteristic values for each of the ECAP signals, determine a targeted range of ECAP characteristic values based on the growth curve which is based on the estimated neural response, which may be a range, a characteristic value of the targeted ECAP signal, and at least one parameter value at least partially defining electrical stimulation therapy to be delivered or offered to the patient. The patient or clinician may further modify the stimulation therapy, for example, based on patient preference or expected battery life, for example.

Although in one example IMD 110 takes the form of an SCS device, in other examples, IMD 110 takes the form of any combination of deep brain stimulation (DBS) devices, peripheral nerve stimulators, implantable cardioverter defibrillators (ICDs), pacemakers, cardiac resynchronization therapy devices (CRT-Ds), left ventricular assist devices (LVADs), implantable sensors, orthopedic devices, or drug pumps, as examples. Moreover, techniques of this disclosure may be used to determine stimulation thresholds (e.g., perception thresholds and detection thresholds) associated any one of the aforementioned IMDs and then use a stimulation threshold to inform the intensity (e.g., stimulation levels) of therapy.

Figure 2A:
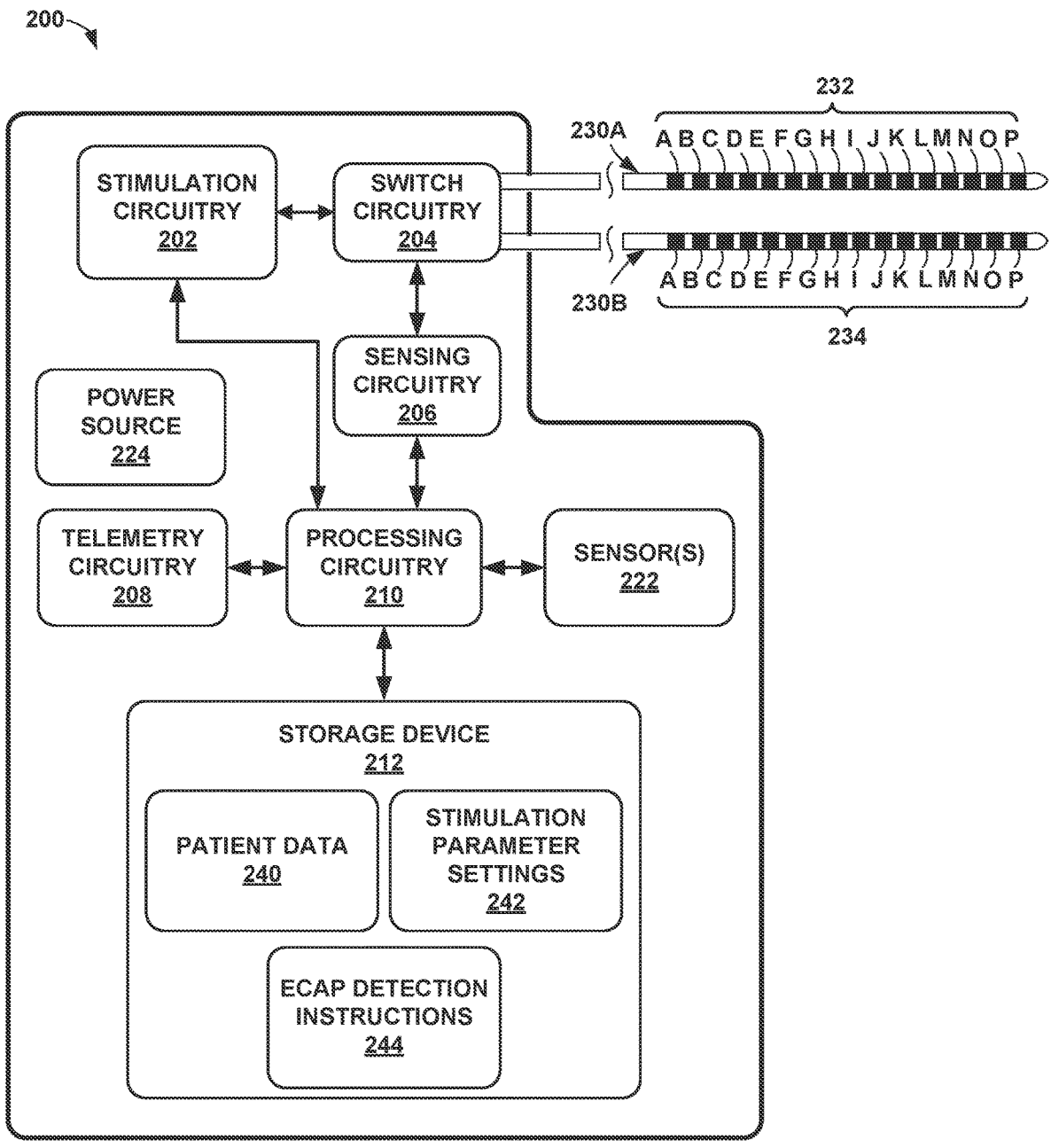
FIG. 2A is a block diagram illustrating an example combination of components of an IMD, in accordance with one or more techniques of this disclosure.

FIG. 2A is a block diagram illustrating an example combination of components of an IMD 200, in accordance with one or more techniques of this disclosure. IMD 200 may be an example of IMD 110 of FIG. 1. In the example shown in FIG. 2A, IMD 200 includes stimulation generation circuitry 202, switch circuitry 204, sensing circuitry 206, telemetry circuitry 208, processing circuitry 210, storage device 212, sensor(s) 222, and power source 224.

In the example shown in FIG. 2A, storage device 212 stores patient data 240, stimulation parameter settings 242, and ECAP detection instructions 244 in separate memories within storage device 212 or separate areas within storage device 212. Patient data 240 may include parameter values, target characteristic values, or other information specific to the patient. In some examples, stimulation parameter settings 242 may include stimulation parameter values for respective different stimulation programs selectable by the clinician or patient for therapy. In this manner, each stored therapy stimulation program, or set of stimulation parameter values, of stimulation parameter settings 242 defines values for a set of electrical stimulation parameters (e.g., a stimulation parameter set), such as a stimulation electrode combination, electrode polarity, current or voltage amplitude, pulse width, pulse rate, and pulse shape, or duty cycle. Storage device 212 may also store ECAP detection instructions 244 that defines values for a set of electrical stimulation parameters configured to elicit a detectable ECAP signal, such as a stimulation electrode combination, electrode polarity, current or voltage amplitude, pulse width, pulse rate, and pulse shape. ECAP detection instructions 244 may also have additional information such as instructions regarding when to deliver control pulses based on the pulse width and/or frequency of the pulses defined in stimulation parameter settings 242, detection windows for detecting ECAP signals, instructions for determining characteristic values from ECAP signals, etc. For example, ECAP detection instructions 244 may define how characteristic values of ECAP signals are to be determined.

Accordingly, in some examples, stimulation generation circuitry 202 generates electrical stimulation signals in accordance with the electrical stimulation parameters noted above. Other ranges of stimulation parameter values may also be useful and may depend on the target stimulation site within patient 105. While stimulation pulses are described, stimulation signals may be of any form, such as continuous-time signals (e.g., sine waves) or the like. Switch circuitry 204 may include one or more switch arrays, one or more multiplexers, one or more switches (e.g., a switch matrix or other collection of switches), or other electrical circuitry configured to direct stimulation signals from stimulation generation circuitry 202 to one or more of electrodes 232, 234, or directed sensed signals from one or more of electrodes 232, 234 to sensing circuitry 206. In other examples, stimulation generation circuitry 202 and/or sensing circuitry 206 may include sensing circuitry to direct signals to and/or from one or more of electrodes 232, 234, which may or may not also include switch circuitry 204.

Sensing circuitry 206 is configured to monitor signals from any combination of electrodes 232, 234. In some examples, sensing circuitry 206 includes one or more amplifiers, filters, and analog-to-digital converters. Sensing circuitry 206 may be used to sense physiological signals, such as ECAP signals. In some examples, sensing circuitry 206 detects ECAPs from a particular combination of electrodes 232, 234. In some cases, the particular combination of electrodes for sensing ECAPs includes different electrodes than a set of electrodes 232, 234 used to deliver stimulation pulses. Alternatively, in other cases, the particular combination of electrodes used for sensing ECAPs includes at least one of the same electrodes as a set of electrodes used to deliver stimulation pulses to patient 105. Sensing circuitry 206 may provide signals to an analog-to-digital converter, for conversion into a digital signal for processing, analysis, storage, or output by processing circuitry 210.

Telemetry circuitry 208 supports wireless communication between IMD 200 and an external programmer (not shown in FIG. 2A) or another computing device under the control of processing circuitry 210. Processing circuitry 210 of IMD 200 may receive, as updates to programs, values for various stimulation parameters such as amplitude and electrode combination, from the external programmer via telemetry circuitry 208. Processing circuitry 210 may store updates to the stimulation parameter settings 242 or any other data in storage device 212. Telemetry circuitry 208 in IMD 200, as well as telemetry circuits in other devices and systems described herein, such as the external programmer, may accomplish communication by radiofrequency (RF) communication techniques. In addition, telemetry circuitry 208 may communicate with an external medical device programmer (not shown in FIG. 2A) via proximal inductive interaction of IMD 200 with the external programmer. The external programmer may be one example of external programmer 150 of FIG. 1. Accordingly, telemetry circuitry 208 may send information to the external programmer on a continuous basis, at periodic intervals, or upon request from IMD 110 or the external programmer.

Processing circuitry 210 may include any one or more of a microprocessor, a controller, a digital signal processor (DSP), an application specific integrated circuit (ASIC), a field-programmable gate array (FPGA), discrete logic circuitry, or any other processing circuitry configured to provide the functions attributed to processing circuitry 210 herein may be embodied as firmware, hardware, software or any combination thereof. Processing circuitry 210 controls stimulation generation circuitry 202 to generate stimulation signals according to stimulation parameter settings 242 and any other instructions stored in storage device 212 to apply stimulation parameter values specified by one or more of programs, such as amplitude, pulse width, pulse rate, and pulse shape of each of the stimulation signals.

In the example shown in FIG. 2A, the set of electrodes 232 includes electrodes 232A-232P, and the set of electrodes 234 includes electrodes 234A-234P. In other examples, a single lead may include 16 electrodes 232 or 234 along a single axial length of the lead. In other examples, a single lead may include more than 8 contacts. In some examples, one or more leads may include electrodes as shown in FIGS. 3A-3D.

Processing circuitry 210 also controls stimulation generation circuitry 202 to generate and apply the stimulation signals to selected combinations of electrodes 232, 234. In some examples, stimulation generation circuitry 202 includes a switch circuit (instead of, or in addition to, switch circuitry 204) that may couple stimulation signals to selected conductors within leads 230, which, in turn, deliver the stimulation signals across selected electrodes 232, 234. Such a switch circuit may be a switch array, switch matrix, multiplexer, or any other type of switching circuit configured to selectively couple stimulation energy to selected electrodes 232, 234 and to selectively sense bioelectrical neural signals of a spinal cord of the patient (not shown in FIG. 2A) with selected electrodes 232, 234.

In other examples, however, stimulation generation circuitry 202 does not include a switch circuit and switch circuitry 204 does not interface between stimulation generation circuitry 202 and electrodes 232, 234. In these examples, stimulation generation circuitry 202 includes a plurality of pairs of voltage sources, current sources, voltage sinks, or current sinks connected to each of electrodes 232, 234 such that each pair of electrodes has a unique signal circuit. In other words, in these examples, each of electrodes 232, 234 is independently controlled via its own signal circuit (e.g., via a combination of a regulated voltage source and sink or regulated current source and sink), as opposed to switching signals between electrodes 232, 234.

Electrodes 232, 234 on respective leads 230 may be constructed of a variety of different designs. For example, one or both of leads 230 may include one or more electrodes at each longitudinal location along the length of the lead, such as one electrode at different perimeter locations around the perimeter of the lead at each of the locations A, B, C, and D. In one example, the electrodes may be electrically coupled to stimulation generation circuitry 202, e.g., via switch circuitry 204 and/or switching circuitry of the stimulation generation circuitry 202, via respective wires that are straight or coiled within the housing of the lead and run to a connector at the proximal end of the lead. In another example, each of the electrodes of the lead may be electrodes deposited on a thin film. The thin film may include an electrically conductive trace for each electrode that runs the length of the thin film to a proximal end connector. The thin film may then be wrapped (e.g., a helical wrap) around an internal member to form the lead 230. These and other constructions may be used to create a lead with a complex electrode geometry.

Although sensing circuitry 206 is incorporated into a common housing with stimulation generation circuitry 202 and processing circuitry 210 in FIG. 2A, in other examples, sensing circuitry 206 may be in a separate housing from IMD 200 and may communicate with processing circuitry 210 via wired or wireless communication techniques. In some examples, one or more of electrodes 232 and 234 are suitable for sensing the ECAPs. For instance, electrodes 232 and 234 may sense the voltage amplitude of a portion of the ECAP signals, where the sensed voltage amplitude, such as the voltage difference between features within the signal, is a characteristic the ECAP signal.

Storage device 212 may be configured to store information within IMD 200 during operation. Storage device 212 may include a computer-readable storage medium or computer-readable storage device. In some examples, storage device 212 includes one or more of a short-term memory or a long-term memory. Storage device 212 may include, for example, random access memories (RAM), dynamic random access memories (DRAM), static random access memories (SRAM), magnetic discs, optical discs, flash memories, or forms of electrically programmable memories (EPROM) or electrically erasable and programmable memories (EEPROM). In some examples, storage device 212 is used to store data indicative of instructions for execution by processing circuitry 210. As discussed above, storage device 212 is configured to store patient data 240, stimulation parameter settings 242, and ECAP detection instructions 244.

In some examples, storage device 212 may store instructions on how processing circuitry 210 can adjust stimulation pulses in response to the determined characteristic values of ECAP signals. For example, processing circuitry 210 may monitor ECAP characteristic values obtained from ECAP signals (or a signal derived from the ECAP signal) to modulate stimulation parameter values (e.g., electrode combination, or increase or decrease stimulation intensity to maintain a target therapeutic effect). In some examples, a target ECAP characteristic value may vary for different situations for a patient, such as different posture states, times of day, activities, etc.

Sensor(s) 222 may include one or more sensing elements that sense values of a respective patient parameter, such as posture state. As described, electrodes 232 and 234 may be the electrodes that sense the characteristic value of the ECAP signal. Sensor(s) 222 may include one or more accelerometers, optical sensors, chemical sensors, temperature sensors, pressure sensors, or any other types of sensors. Sensor(s) 222 may output patient parameter values that may be used as feedback to control delivery of therapy. For example, sensor(s) 222 may indicate patient activity, and processing circuitry 210 may increase the frequency of control pulses and ECAP sensing in response to detecting increased patient activity. In one example, processing circuitry 210 may initiate control pulses and corresponding ECAP sensing in response to a signal from sensor(s) 222 indicating that patient activity has exceeded an activity threshold. Conversely, processing circuitry 210 may decrease the frequency of control pulses and ECAP sensing in response to detecting decreased patient activity. For example, in response to sensor(s) 222 no longer indicating that the sensed patient activity exceeds a threshold, processing circuitry 210 may suspend or stop delivery of control pulses and ECAP sensing. In this manner, processing circuitry 210 may dynamically deliver control pulses and sense ECAP signals based on patient activity to reduce power consumption of the system when the electrode-to-neuron distance is not likely to change and increase system response to ECAP changes when electrode-to-neuron distance is likely to change. IMD 200 may include additional sensors within the housing of IMD 200 and/or coupled via one of leads 130 or other leads. In addition, IMD 200 may receive sensor signals wirelessly from remote sensors via telemetry circuitry 208, for example. In some examples, one or more of these remote sensors may be external to patient (e.g., carried on the external surface of the skin, attached to clothing, or otherwise positioned external to patient 105). In some examples, signals from sensor(s) 222 indicate a position or body state (e.g., sleeping, awake, sitting, standing, or the like), and processing circuitry 210 may select target ECAP characteristic values according to the indicated position or body state.

Power source 224 is configured to deliver operating power to the components of IMD 200. Power source 224 may include a battery and a power generation circuit to produce the operating power. In some examples, the battery is rechargeable to allow extended operation. In some examples, recharging is accomplished through proximal inductive interaction between an external charger and an inductive charging coil within IMD 200. Power source 224 may include any one or more of a plurality of different battery types, such as nickel cadmium batteries and lithium ion batteries.

Figure 2B:
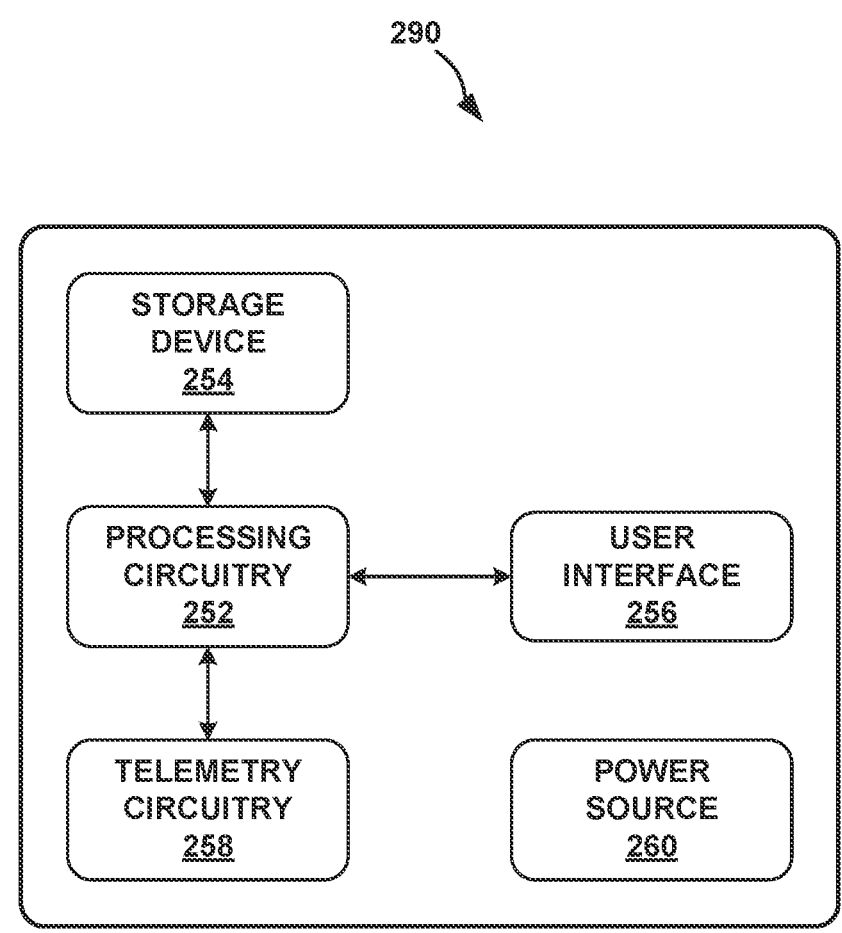
FIG. 2B is a block diagram illustrating an example combination of components of an example external programmer, in accordance with one or more techniques of this disclosure.

FIG. 2B is a block diagram illustrating an example combination of components of an example external programmer 290. External programmer 290 may be an example of external programmer 150 of FIG. 1. Although external programmer 290 may generally be described as a hand-held device, external programmer 290 may be a larger portable device or a more stationary device. In addition, in other examples, external programmer 290 may be included as part of an external charging device or include the functionality of an external charging device. As illustrated in FIG. 2B, external programmer 290 may include processing circuitry 252, storage device 254, user interface 256, telemetry circuitry 258, and power source 260. Storage device 254 may store instructions that, when executed by processing circuitry 252, cause processing circuitry 252 and external programmer 290 to provide the functionality ascribed to external programmer 290 throughout this disclosure. Each of these components, circuitry, or modules, may include electrical circuitry that is configured to perform some, or all of the functionality described herein. For example, processing circuitry 252 may include processing circuitry configured to perform the processes discussed with respect to processing circuitry 252.

In general, external programmer 290 includes any suitable arrangement of hardware, alone or in combination with software and/or firmware, to perform the techniques attributed to external programmer 290, and processing circuitry 352, user interface 356, and telemetry circuitry 358 of external programmer 290. In various examples, external programmer 290 may include one or more processors, such as one or more microprocessors, DSPs, ASICs, FPGAs, or any other equivalent integrated or discrete logic circuitry, as well as any combinations of such components. External programmer 290 also, in various examples, may include a storage device 254, such as RAM, ROM, PROM, EPROM, EEPROM, flash memory, a hard disk, a CD-ROM, including executable instructions for causing the one or more processors to perform the actions attributed to them. Moreover, although processing circuitry 252 and telemetry circuitry 258 are described as separate modules, in some examples, processing circuitry 252 and telemetry circuitry 258 are functionally integrated. In some examples, processing circuitry 252 and telemetry circuitry 258 correspond to individual hardware units, such as ASICs, DSPs, FPGAs, or other hardware units.

Storage device 254 (e.g., a storage device) may store instructions that, when executed by processing circuitry 252, cause processing circuitry 252 and external programmer 290 to provide the functionality ascribed to external programmer 290 throughout this disclosure. For example, storage device 254 may include instructions that cause processing circuitry 252 to obtain a parameter set from memory, select a spatial electrode pattern, or receive a user input and send a corresponding command to IMD 200, or instructions for any other functionality. In addition, storage device 254 may include a plurality of programs, where each program includes a parameter set that defines therapy stimulation or control stimulation. Storage device 254 may also store data received from a medical device (e.g., IMD 110). For example, storage device 254 may store ECAP related data recorded at a sensing module of the medical device, and storage device 254 may also store data from one or more sensors of the medical device.

User interface 256 may include a button or keypad, lights, a speaker for voice commands, a display, such as a liquid crystal (LCD), light-emitting diode (LED), or organic light-emitting diode (OLED). In some examples the display includes a touch screen. User interface 256 may be configured to display any information related to the delivery of electrical stimulation, identified posture states, sensed patient parameter values, or any other such information. User interface 256 may also receive user input (e.g., indication of when the patient perceives a stimulation pulse) via user interface 256. The input may be, for example, in the form of pressing a button on a keypad or selecting an icon from a touch screen. The input may request starting or stopping electrical stimulation, the input may request a new spatial electrode pattern or a change to an existing spatial electrode pattern, of the input may request some other change to the delivery of electrical stimulation.

Telemetry circuitry 258 may support wireless communication between the medical device and external programmer 290 under the control of processing circuitry 252. Telemetry circuitry 258 may also be configured to communicate with another computing device via wireless communication techniques, or direct communication through a wired connection. In some examples, telemetry circuitry 258 provides wireless communication via an RF or proximal inductive medium. In some examples, telemetry circuitry 258 includes an antenna, which may take on a variety of forms, such as an internal or external antenna.

Examples of local wireless communication techniques that may be employed to facilitate communication between external programmer 290 and IMD 110 include RF communication according to the 802.11 or Bluetooth® specification sets or other standard or proprietary telemetry protocols. In this manner, other external devices may be capable of communicating with external programmer 290 without needing to establish a secure wireless connection. As described herein, telemetry circuitry 258 may be configured to transmit a spatial electrode movement pattern or other stimulation parameter values to IMD 110 for delivery of electrical stimulation therapy. Although IMD 110 may determine characteristic values for ECAP signals and control the adjustment of stimulation parameter values in some examples, programmer 290 may perform these tasks alone or together with IMD 110 in a distributed function.

In some examples, selection of stimulation parameters or therapy stimulation programs are transmitted to the medical device for delivery to a patient (e.g., patient 105 of FIG. 1). In other examples, the therapy may include medication, activities, or other instructions that patient 105 must perform themselves or a caregiver perform for patient 105. In some examples, external programmer 290 provides visual, audible, and/or tactile notifications that indicate there are new instructions. External programmer 290 requires receiving user input acknowledging that the instructions have been completed in some examples.

User interface 256 of external programmer 290 may also be configured to receive an indication from a clinician instructing a processor of the medical device to update one or more therapy stimulation programs or to update the target characteristic values for ECAP signals. Updating therapy stimulation programs and target characteristic values may include changing one or more parameters of the stimulation pulses delivered by the medical device according to the programs, such as amplitude, pulse width, frequency, and pulse shape of the pulses and/or control pulses, and/or or electrode combination. User interface 256 may also receive instructions from the clinician commanding any electrical stimulation, including therapy stimulation and control stimulation to commence or to cease.

Power source 260 is configured to deliver operating power to the components of external programmer 290. Power source 260 may include a battery and a power generation circuit to produce the operating power. In some examples, the battery is rechargeable to allow extended operation. Recharging may be accomplished by electrically coupling power source 260 to a cradle or plug that is connected to an alternating current (AC) outlet. In addition, recharging may be accomplished through proximal inductive interaction between an external charger and an inductive charging coil within external programmer 290. In other examples, traditional batteries (e.g., nickel cadmium or lithium ion batteries) may be used. In addition, external programmer 290 may be directly coupled to an alternating current outlet to operate.

The architecture of external programmer 290 illustrated in FIG. 2B is shown as an example. The techniques as set forth in this disclosure may be implemented in the example external programmer 290 of FIG. 2B, as well as other types of systems not described specifically herein. Nothing in this disclosure should be construed so as to limit the techniques of this disclosure to the example architecture illustrated by FIG. 2B.

The techniques herein describe testing different electrode combination for high-density leads. FIGS. 3A and 3B-3D are a variety of electrode combinations 300A, 300B which can be tested with stimulation, and the resulting ECAP signal may be determined and recorded. The characteristics of the ECAP signal for the various combinations may be evaluated and used to determine a suitable electrode combination. In one or more examples, the multiple different electrode combinations include electrode combinations having more than eight electrodes. In some examples, a plurality of stimulation pulses to are delivered by at least one stimulation electrode combination, and the ECAP signal is recorded using different sensing electrode combinations. In some examples, one electrode combination is selected based on the ECAP signal information recorded from the multiple different sensing electrode combinations.

Figure 3A:
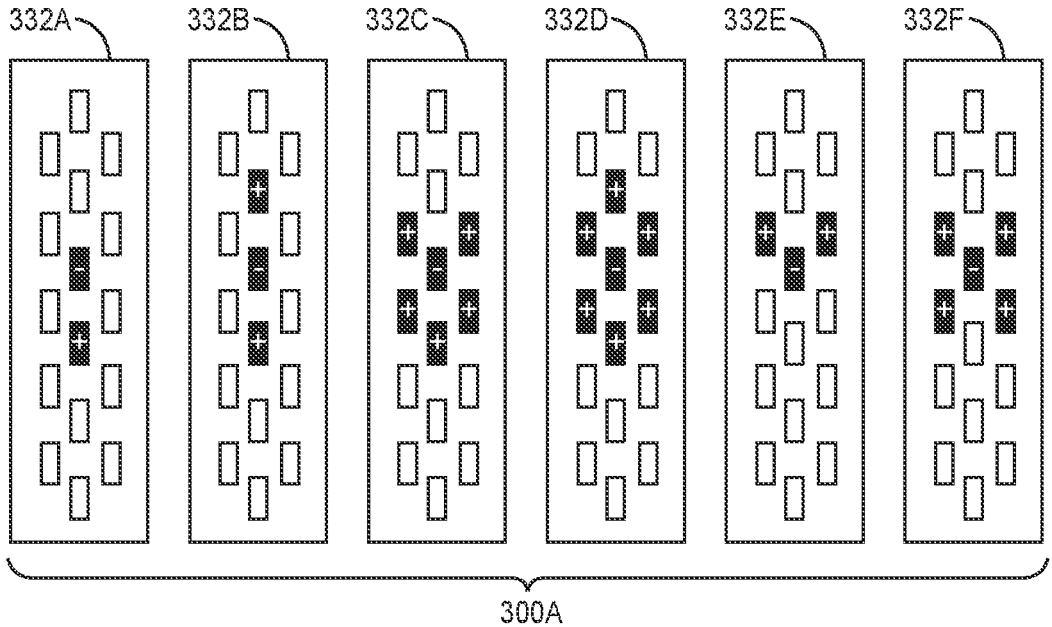
FIG. 3A is a conceptual diagram illustrating a series of electrode combinations, in accordance with one or more techniques of this disclosure.

FIG. 3A illustrates example electrode combinations 300A, including electrode combinations 332A, 332B, 332C, 332D, 332E, 332F for a 5-6-5 paddle lead. In the examples shown in FIG. 3A, the dark rectangles indicate selected electrodes for anode (+), indicated in FIG. 3A as a rectangle having a "+" symbol, and cathode (−), indicated in FIG. 3A as a rectangle having a "−" symbol. In some examples, the electrode combination may be a sensing electrode combination. The electrode combinations 332A, 332B, 332C, 332D, 332E, 332F may each be used to record ECAP signal information, and the information may be analyzed to determine a preferred electrode combination. In one or more examples, an electrode combination may include a bipole electrode combination 332A. In one or more examples, an electrode combination may include a guarded cathode electrode combination 332B, for example where two anodes may be disposed on each side of a cathode or bracketing the cathode. In one or more examples, an electrode combination may include a guarded bipole electrode combination 332C, for example where two anodes may be disposed on a first side of a cathode, and two or more anodes may be disposed on a second side of the cathode. In one or more examples, an electrode combination may include a guarded tripole electrode combination 332D, for example where three anodes may be disposed on each side of a cathode or bracketing the cathode. In one or more examples, an electrode combination may include a single transverse electrode combination 332E, for example where two anodes may be disposed at a first side of a cathode instead of any anodes on another side of the cathode. In one or more examples, an electrode combination may include a second transverse electrode combination 332F, where two anodes may be disposed on a first side of a cathode, and two anodes may be disposed on a second side of the cathode. These electrode combinations are examples where anodes partially or fully surround a cathode. Although FIG. 3A illustrates example paddle lead having a number of electrodes as shown in the figures, other paddle leads with more electrodes, fewer electrodes, or different electrode array designs may be used instead. Alternatively, other leads, such as cylindrical leads, leads with different electrodes disposed at different positions around the perimeter of the lead (e.g., different partially circumferential electrodes), or any other electrode carrying devices may provide different electrode combinations.

Figures 3B, 3C, 3D:
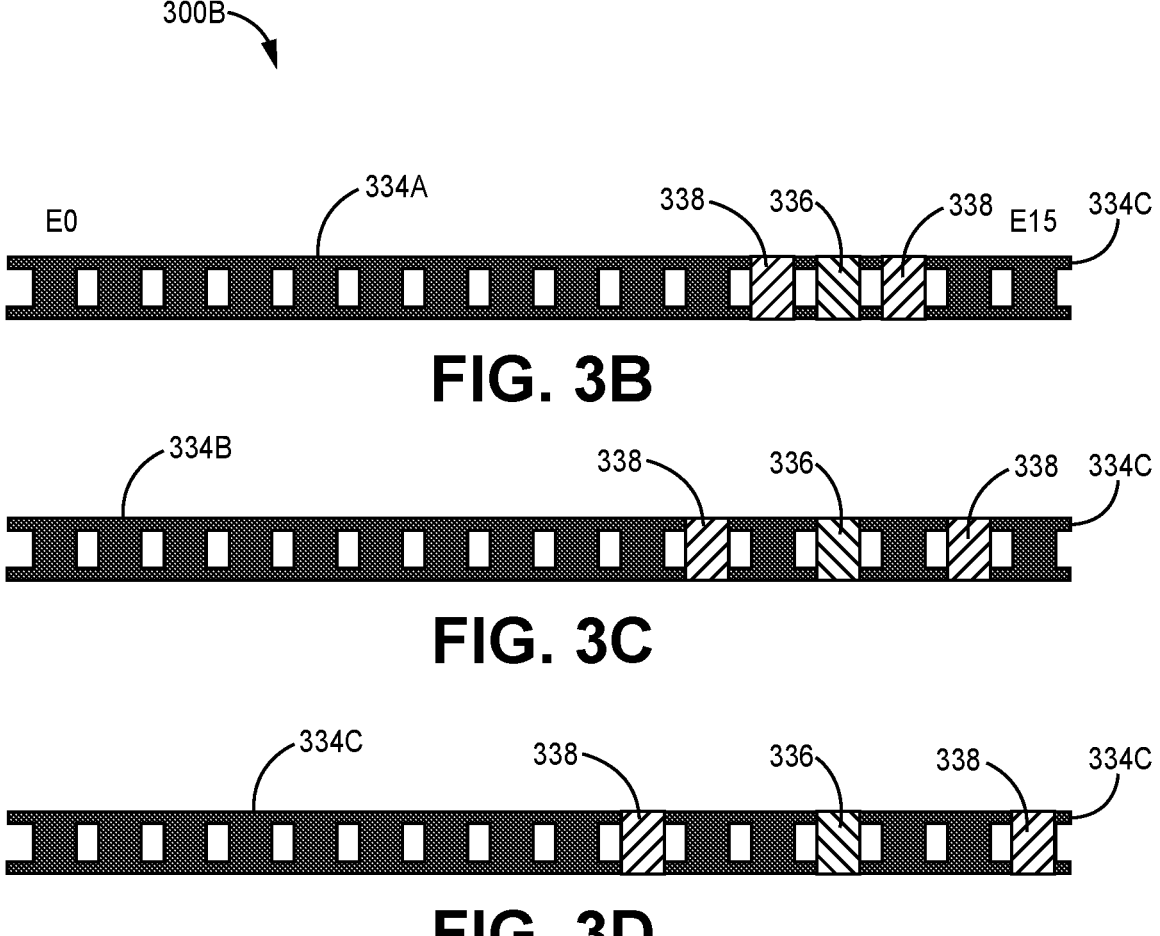
FIG. 3B is a conceptual diagram illustrating an electrode combination, in accordance with one or more techniques of this disclosure.
FIG. 3C is a conceptual diagram illustrating an electrode combination, in accordance with one or more techniques of this disclosure.
FIG. 3D is a conceptual diagram illustrating an electrode combination, in accordance with one or more techniques of this disclosure.

FIG. 3B-3D illustrates additional examples of three different electrode combinations 334A, 334B, 334C, for example electrode combination with a narrow (FIG. 3B), intermediate (FIG. 3C) and wide (FIG. 3D) tripolar electrode combinations. In FIG. 3B, the dark gray electrode (336) may be an input of a biopotential amplifier, and the lighter gray electrode (338) may be connected to another input. Put another way, electrode 336 is a different polarity from electrodes 338. In the examples shown in FIG. 3B-3D, black contacts are not in use. Wide bipolar spacings may also be possible with high density leads, such as shown in the combination 334A where recording between electrode 15 and 10 occurs.

The stimulation is provided while the processor iterates through different sensing electrode combinations. The resulting ECAP signal and related stimulation artifact are measured during stimulation. The stimulation is provided while the processor iterates through the electrode combinations until, in some examples an aspect of the stimulation artifact satisfies a threshold, such as until the amplitude of the stimulation artifact is under a threshold and/or sensitivity to neural activation satisfies a threshold, for example the amplitude of neural activation exceeds a threshold. In some examples, the aspect of the stimulation artifact may include amplitude of one or more peaks, amplitude between peaks, differences between ECAP peaks (See FIG. 4B), or area under a curve. The processor may recommend or automatically implement an electrode combination that results in a lower or lowest amplitude of the stimulation artifact and/or higher or highest amplitude of the neural activation from the measured samples for the electrode combinations. In some examples, the processor may present recommended sensing configurations for confirmation by user input. In some examples, the processor may present electrode combinations and their corresponding artifact and/or ECAP values for selection by the user.

Figure 4A:
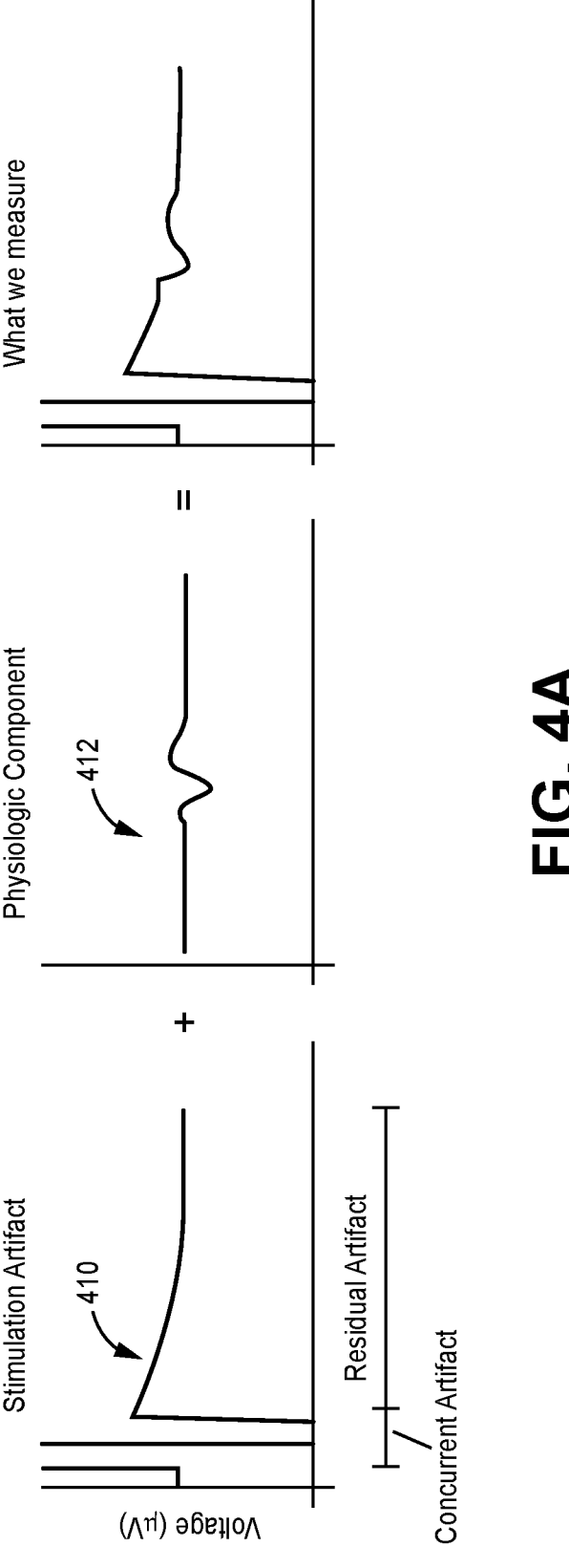
FIG. 4A is a graph of example sensed evoked compound action potentials (ECAPs), in accordance with one or more techniques of this disclosure.

Evoked biopotentials recorded in a body of a patient, such as evoked compound action potential (ECAP) generally consists of two elements: stimulation artifact 410 and an actual electrophysiologic component 412, as shown in FIG. 4A. For ECAPs measured in the spinal cord, characteristics of the ECAP (such as the amplitude, timing, and morphology) may be set by many factors such as, but not limited to, separation between the stimulating and recording electrode, spacing between the recording electrodes, dimensions and composition of the electrodes, stimulation parameter set (electrode selection, frequency, amplitude, and pulse width), location of the electrodes with respect to anatomical structures such as the laminar bone, midline vs. lateral placement, and the dorsal roots, thickness of the cerebrospinal fluid, and neurophysiologic state of the patient. In general, it may be preferred to maximize the electrophysiologic component of the ECAP while minimizing the stimulation artifact. In some examples, the system or clinician may prioritize greater electrophysiologic component signal amplitude or prioritize reduced amplitude of the stimulation artifact.

Figure 4B:
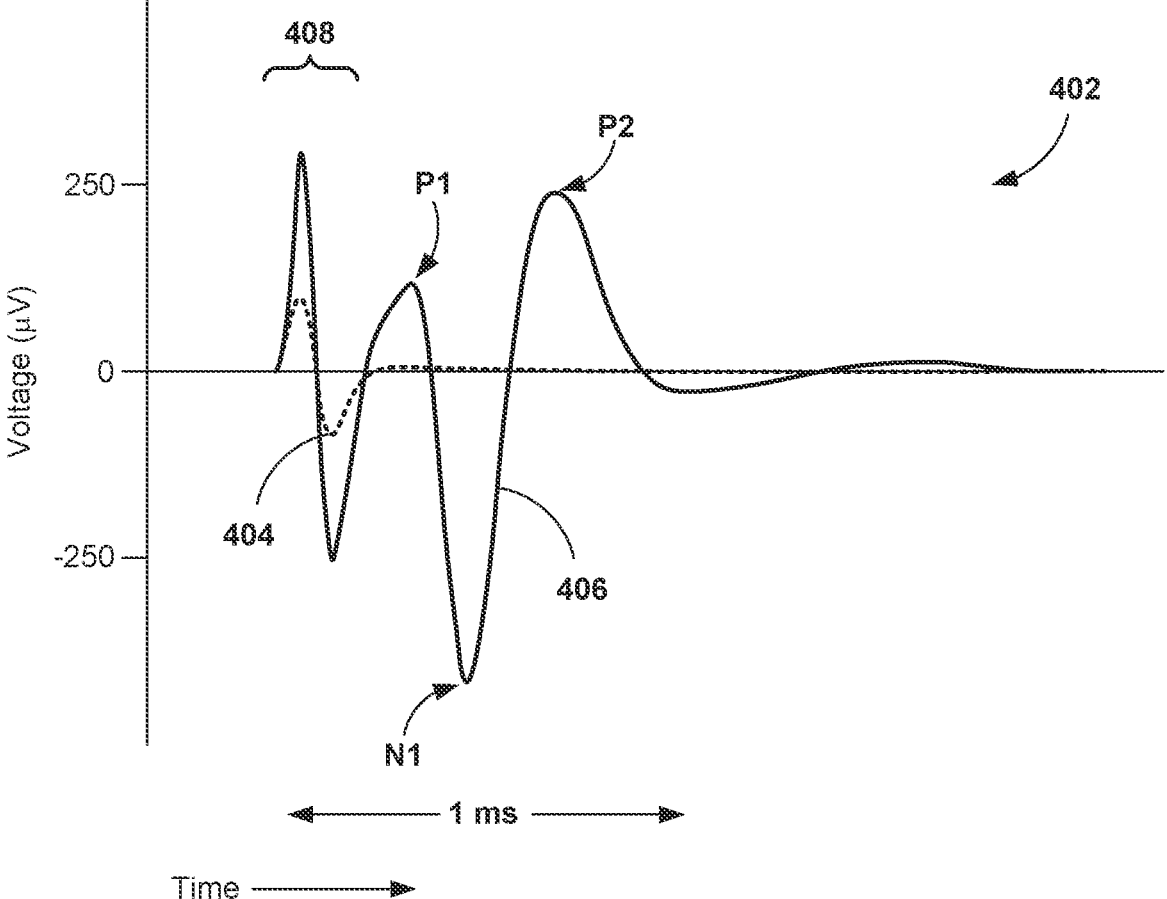
FIG. 4B is a graph of example evoked compound action potentials (ECAPs) sensed for respective stimulation pulses, in accordance with one or more techniques of this disclosure.

FIG. 4B is a graph 402 of example evoked compound action potentials (ECAPs) sensed for respective stimulation pulses, in accordance with one or more techniques of this disclosure. As shown in FIG. 4B, graph 402 shows example ECAP signal 404 (dotted line) and ECAP signal 406 (solid line). In some examples, each of ECAP signals 404 and 406 are sensed from stimulation pulses that were delivered from a guarded cathode, where the control pulses are bi-phasic pulses including an interphase interval between each positive and negative phase of the pulse. In some such examples, the guarded cathode includes stimulation electrodes located at the end of an 8-electrode lead while two sensing electrodes are provided at the other end of the 8-electrode lead. ECAP signal 404 illustrates the voltage amplitude sensed as a result from a sub-detection threshold stimulation pulse. In other words, the stimulation pulse did not elicit a detectable ECAP signal in ECAP signal 404. Peaks 408 of ECAP signal 404 are detected and represent the artifact of the delivered stimulation pulse. However, no propagating signal is detected after the artifact in ECAP signal 404 because the stimulation pulse was sub-detection threshold (e.g., the intensity of the stimulation pulse was insufficient to cause nerve fibers to depolarize and generate a detectable ECAP signal).

In contrast to ECAP signal 404, ECAP signal 406 represents the voltage amplitude detected from a supra-detection threshold stimulation pulse. Peaks 408 of ECAP signal 406 are detected and represent the artifact of the delivered stimulation pulse. After peaks 408, ECAP signal 406 also includes electrophysiological components such as peaks P1, N1, and P2, which are three typical peaks representative of propagating action potentials from an ECAP. In some examples, the techniques described herein include selection of an electrode combination which maximizes the electrophysiological components of the ECAP signal. The example duration of the artifact and peaks P1, N1, and P2 is approximately 1 millisecond (ms). The time between two points in the ECAP signal may be referred to as a latency of the ECAP and may indicate the types of fibers being captured by the control pulse. ECAP signals with lower latency (i.e., smaller latency values) indicate a higher percentage of nerve fibers that have faster propagation of signals, whereas ECAP signals with higher latency (i.e., larger latency values) indicate a higher percentage of nerve fibers that have slower propagation of signals. Other characteristics of the ECAP signal may be used in other examples.

The amplitude of the ECAP signal (e.g., peaks within the ECAP signal) generally increases with increased amplitude of the stimulation pulse, as long as the pulse amplitude is greater than threshold such that nerves depolarize and propagate the signal. The target ECAP characteristic (e.g., the target ECAP amplitude) may be determined from an ECAP signal associated with an estimated neural response detected from pulses delivering therapy to patient 105. The ECAP signal thus is representative of the distance between the stimulation electrodes and the nerves appropriate for the stimulation parameter values of the pulses delivered at that time. In some examples, the target ECAP characteristic may include one in which a stimulation artifact is minimized and/or a neural activation is maximized.

In some examples, processing circuitry 210 or other devices may be configured to determine a characteristic value for an ECAP signal, for example, from multiple different features of one or more signals associated with the ECAP signal. The characteristic value of the ECAP signal may be determined by removing an artifact from the ECAP signal using the processing circuitry. These different features may be incorporated into an average, weighted average, or other combination that represents the relative action potentials of the ECAP signal. Processing circuitry 210 may determine the characteristic value from different features of the same signal, such as the amplitude difference between two peaks in the ECAP signal and the amplitude difference between two difference peaks in the ECAP signal. As another example of features from the same signal, processing circuitry 210 may determine the characteristic value based on an average of two different peaks in the second derivative signal. Alternatively, processing circuitry 210 may determine the characteristic value of the ECAP signal from features obtained from different signals. For example, processing circuitry 210 may determine the difference between the minimum and maximum values of the first derivative of the ECAP signal on either side of the P2 peak, determine the maximum value of the second derivative of the ECAP signal, and combine each of these factors into a single characteristic value of the ECAP signal. This single characteristic value of the ECAP signal may be referred to as a composite characteristic value because it is a composite of several different factors derived from the ECAP signal in order to obtain a more complete representation of the ECAP signal.

In one or more examples, the ECAP characteristic values may be determined after subtracting the artifact, to the extent an artifact may be present during some portion of the sensed ECAP signal. In some examples, that artifact may be modeled as a sum of exponential and a linear component. In another example, the artifact may be modeled sufficiently by either an exponential or a linear component alone. In order to fit the artifact to the response for the growth curve, several methods may be used. In one or more examples, the method may include estimating a minimum in the error function between the artifact model and the measured response. For example, if parameters of the function are P (e.g., time constant of the exponential, gain and linear slope and offset), the error function may be:

$$Err(P) = E[E(t) - A(P, t)]$$

The optimal fit is to find $P_{opt}$ where the error Err(P) is minimized. The ECAP characteristic value may be determined the recording E(t) as:

$$ECAP(t) = E(t) - A(P_{opt}, t)$$

A common error function Err is something like a norm-2, which is defined as $$E = sqrt(sum\_t)((E(t) - A(P, t)) \wedge 2)$$

An example model A(P,t) with four parameters is as follows:

$$A(P, t) = \exp(-t/P(1)) * P(2) + t * P(3) + P(4)$$

In one or more examples, the error function may be modified by a weight function W(t), where W(t) is high for instances where the neural response is low, for example in the first region. For example, the W function may be high for t early in the measured waveform E(t) (for example prior to neural response developing) and low where the neural response can be high. In some examples, W(t) can be higher after the response.

$$E[P] = sqrt(sum\_t(W(t) * (E(t) - A(P, t)) \wedge 2)$$

In this way, the model can be fit more specifically to the artifact, and not to the neural response, for example for the first region. The weight can thus be adjusted by the system to reduce the effect of any stimulation artifact while maintaining ECAP components to the signal. Note that for this analysis a uniform W (e.g., the weight) may be used so this feature may be optional.

It is also understood that once the time constant P(1) is estimated, the rest of parameters may be solved. For instance, in some examples, if M is defined as a matrix with rows [exp(−t/P(1))t 1] and Wm is a matrix with diagonal equal to W, then parameter P(2) to P(4) may be:

$$P_{end} = (A' * \mathrm{diag}(W') * \mathrm{diag}(W) * A) \backslash (A' * \mathrm{diag}(W') * \mathrm{diag}(W) * \mathrm{data})$$

Figure 4C:
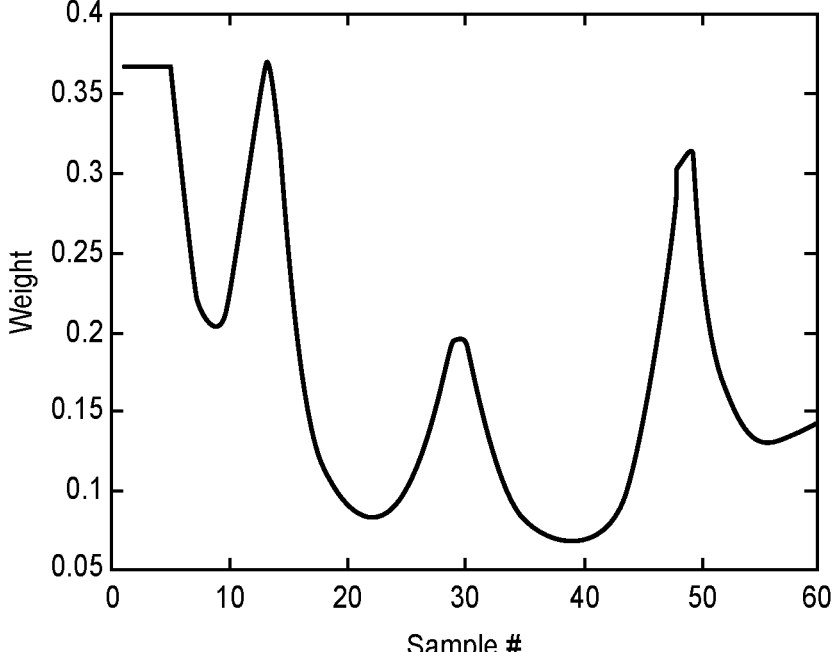
FIG. 4C is a graph of an example weight array W for multiple samples, in accordance with one or more techniques of this disclosure.

In the above table, the "\" operator is a matrix inversion operator and diag(W) transforms the weight vector of length n to a matrix of weight n with contents of W. An example weight array W is shown in FIG. 4C. Features of interest in W may include high starting level (where most of the artifact is contained but ECAP response is low), and low weight for features which may contain the main ECAP energy (e.g., around sample 20 and 40). In addition, weight might contain peaks corresponding to typical transition regions (e.g., peak around sample 11 or sample 30).

For real-time systems, the matrix multiplication operation may be fairly efficient. Thus, there may be an adaptive procedure to solve for P(1) (for example by back-propagation of error method) and then an analytic method to solve for P(2) to P(4). In one or more examples, if the artifact can change fairly rapidly, speed of back-propagation kind of algorithm may be adjusted depending on the error term (e.g., large errors can lead to faster adaptation of P(1)). In some examples, either P(1) or range of P(1) can be estimated using equipment external to the implant, such as a clinician programmer or a patient programmer.

For certain weight functions, the equation for $P_{end}$ can be a sparse equation and can be reduced to a non-FIR filter model. In addition, several P(1) candidates may be evaluated and the smallest one can be selected for the algorithm. Another alternative may be to determine evaluate several P(1) candidates, pick the minimum one, but to utilize the adjacent near-by measurements to fit a curve, e.g., a parabola, to determine more precisely the location of the minimum. In this way, only accuracy can be improved with fewer evaluations.

In one or more examples, the artifact may be removed from the ECAP using various methods, including, but not limited to, a standard method, artifact model method, high-pass filter method, or a correlation method, where each method uses the processing circuitry to determine the ECAP characteristic value such as neural activation.

In using the standard method (SM) to determine ECAP characteristic value, waveforms $V_i(t)$ may be low-pass filtered (Kaiser filter, 11 tap, 4.5 kHz) to further band-limit and reduce asynchronous noise. In one or more examples, ECAP amplitude may be subsequently (calculated) estimated as a difference (e.g., in amplitude, such as in µV) between the P2 and N1 features of the ECAP. In one or more examples, N1 may be defined as the minimum amplitude of the filtered waveform in the temporal window from 0.3 to 0.6 milliseconds (ms), while P2 may be defined as the maximum amplitude in the temporal window from 0.7 to 1.1 ms. These windows of time may be set given the anticipated latencies and morphological characteristics of the ECAP. The latencies may be a function of the spacing between the stimulating and recording electrodes, along with the expected conduction velocity of ECAPs in the spinal cord. In cases of large artifact that starts positive and decays overtime, it is possible that the N1 is greater than P2, where the N1-P2 may be computed to be negative.

The processing circuitry 210 may also, or alternatively, use an artifact model (AM) to determine a ECAP characteristic value. In one or more examples, the stimulation artifact may be composed of two decaying exponentials with different time constants. In one or more examples, over a relatively short post-stimulation window for estimating spinal ECAPS, for example, 1.5 ms, artifact may be suitably modeled as the sum of a single exponential plus a linear component, may more accurately estimate ECAP amplitude. If $V_i(t)$ is the recorded voltage waveform after averaging, the estimate of artifact A(t) may be obtained by optimally fitting the following equation to data $V_i(t)$:

$$A(t) = c_1 \exp(-t/\tau) + c_2 t + c_3$$

The fit may be performed by determining the minimum in the following error function over parameters c1, c2, c3, and τ:

$$E(c_1, c_2, c_3, \tau) = \sum_t (V(t) - A(t))^2$$

To solve this optimization problem, τ may be varied from 50 to 800 ρs in 100 logarithmic steps. For each τ, E(τ) may be determined by solving the following closed-form matrix equation:

$$M = \begin{bmatrix} \exp\left(-\dfrac{t_0}{\tau}\right) & t_0 & 1 \\ \exp\left(-\dfrac{2t_0}{\tau}\right) & 2t_0 & 1 \\ \cdots & \cdots & \cdots \end{bmatrix}$$

$$C = (M'M)\backslash(M'V)$$
$$E(t) = Norm(V - M\ C)$$

In the above equation, $t_0$ may be the sampling period, C is a 3×1 vector of optimal c coefficients, V may be a vector composed of measured samples V(t), and Norm may represent a norm-2 operation. Optimal τ may be determined to be one that produced the smallest E(τ); the equation above was utilized to compute the C coefficients. After the artifact model is determined, the N1-P2 amplitude may be calculated or estimated from the denoised waveform V(t)-A(t) using the same N1 and P2 windows as in the standard method.

In one or more examples, the processing circuitry 210 may also, or alternatively, use a high-pass filter (HP) method. For example, the stimulation artifact may contain lower-frequency content relative to the ECAP in the later portion of the biopotential recording (e.g., greater than 0.6 milliseconds (ms) after the end of the stimulation pulse). As such, another approach for mitigating the stimulation artifact overlapping the ECAP may be application of a high pass or differentiator filter. Such a filter may have the following benefits. The first peak response of the differentiator occurs at the high-slope transition of the ECAP from N1 to P2. This response may be delayed relative to N1, the first feature of the ECAP used by the SM to estimate the ECAP, and results beneficially in extra temporal isolation between the signal and the artifact with the differentiator. In addition, a simple differentiator may be implemented in a very computationally efficient manner, an important consideration for battery powered implantable medical devices.

A comb filter with response $1-z^2$ may be utilized as a differentiator for the acquired biopotentials. After application of the differentiator filter, the waveform may be smoothed (Kaiser, FIR II tap filter: cutoff 4.5 kHz). The ECAP response may be computed as the difference between the maximum output in the temporal window from approximately 0.6 to 0.85 ms to the minimum output in the window from approximately 0.9 to 1.125 ms. The temporal windows may be set using similar considerations to those employed with the standard method.

The processing circuitry 210 may also, or alternatively, use a correlation method (CM) which estimates spinal cord activation by correlating the acquired biopotential with a synthesized filter template, T(t). Specifically, the neural response may be computed as:

$$N_i = \sum_t T(t) * V_i(t - \Delta)$$

The template used here may have a mathematical expression of $T(t)=B(t) \sin(4\pi t/1.3)/N$ where, t is time in ms, B(t) is the Bartlett window, and N is the normalization factor, $N=\mathrm{sum}(B(t)2 \sin(4\pi t/1.3)2)$ over a 1.3 ms window, for example. The template may approximate the morphology of a typical ECAP signal. A duration of 1.3 ms may be used to optimize the match of the template with the observed response. The template may be orthogonal to the first three components of a Taylor expansion of the artifact waveform, namely the constant term, the linear term and the quadratic term. Thus, when the template is applied to a waveform containing both neural response and artifact, the artifact component may be reduced. However, variable latencies in neural responses routinely occur due to the differences in conduction velocities across subjects and delay in action potential initiation across stimulation levels or pulse width. The template may be matched to the neural recording and Fourier techniques may be utilized accordingly to compute the optimal delay, $\Delta$.

$$A_i = \sum_t \frac{B(t) \sin(4\pi t/1.3)}{N} * V_i(t)$$

$$A_r = \sum_t \frac{B(t) \cos(4\pi t/1.3)}{N} * V_i(t)$$

$$\Delta \text{ (ms)} = -\left(\frac{L(A_i + A_R \ 1j)}{4 \ \pi}\right) 1.3$$

In some examples, to account for variability in neural response latencies, while avoiding non-physiological shifts in the response, the system may prevent $\Delta$ from decreasing below 0 or increasing above 0.18 ms.

Figure 5A:
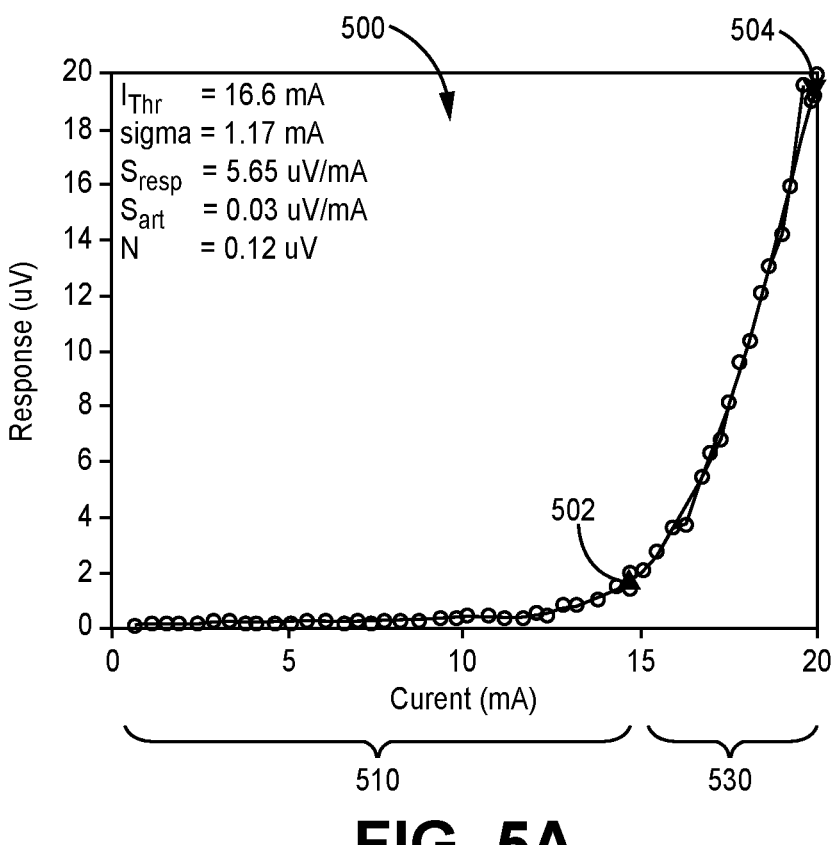
FIG. 5A is an example growth curve of characteristic values for sensed ECAPs, in accordance with one or more techniques of this disclosure.
Figure 5B:
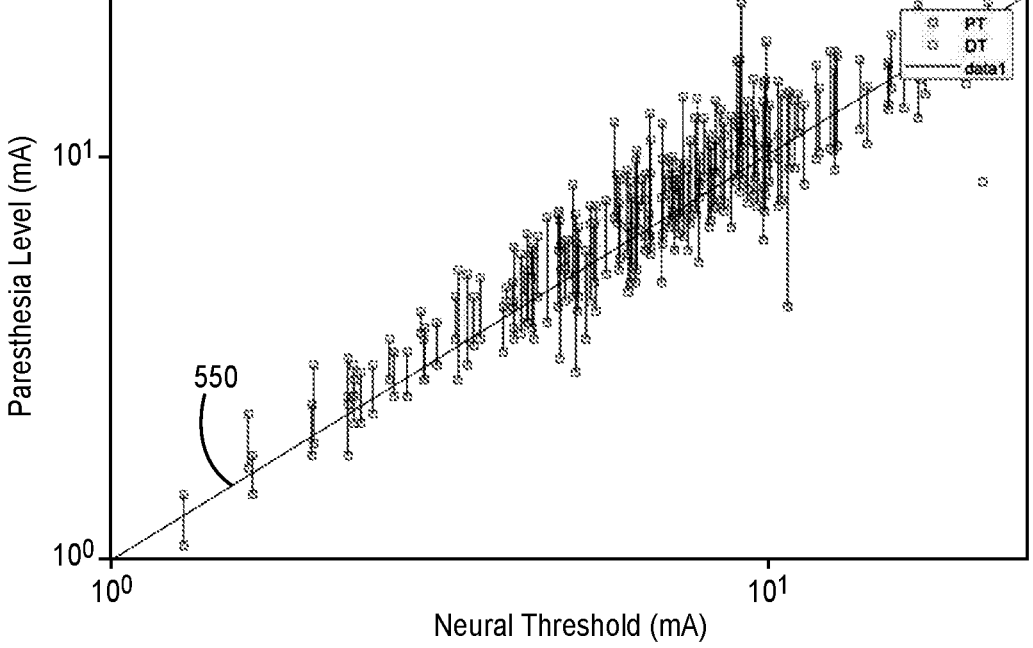
FIG. 5B is a graph of data of the perception threshold and neural threshold, in accordance with one or more techniques of this disclosure.

Once the ECAP characteristic value has been determined, the value may be used to determine an estimated neural threshold. A patient threshold of stimulation (for example, a perception threshold that represents the minimal stimulation current that causes a patient to feel the stimulation) may be correlated to the neural threshold. For example, FIG. 5B shows a relationship between neural threshold and perception threshold as amplitude increases. As shown in FIG. 5B, the patient threshold of stimulation is tightly correlated to neural threshold, where the best fit line is shown at 550. In one or more examples, a growth curve, or a correlation curve, may be developed which may define a relationship between ECAP characteristic values for different stimulation amplitudes (FIG. 5A). Processing circuitry 210 may generate the growth curve by controlling stimulation circuitry to deliver stimulation pulses sweeping the stimulation amplitude (e.g., iteratively increasing the amplitude) and/or testing different electrode combinations (FIGS. 3A, 3B) to sense respective ECAP signals and obtain ECAP characteristic values (e.g., data) which represents an estimated neural response. In some examples, selecting a preferred electrode combination using, for example, ECAP characteristic values, may improve determination of the neural threshold. In one or more embodiments, a storage device may store data which may define a correlation curve (e.g., a growth curve) defining a relationship between the ECAP characteristic values and stimulation amplitude. The system may determine the estimated neural thresholds based on this correlation curve. The estimated neural threshold may represent the estimated stimulation amplitude at which the patient response would transition from sub-perception, to perception of stimulation. The system may set an initial amplitude for stimulation based on the estimated neural threshold or set a target ECAP value for therapy using the estimated neural threshold (e.g., below, at, or above the neural threshold of the patient). In some examples, near the neural threshold of the patient, there may be a substantial curvilinear component, such as the beginning of an inflection portion of the correlation curve. In one or more examples, a non-physiologic component of the response manifest occasionally below the neural threshold. In some examples, the response can grow-linearly with increasing current and may be related to the residual artifact.

In one or more examples, as shown in FIG. 5A, the growth curve 500 from ECAP signals detected at the spinal cord may include a first region 510, which may be substantially linear. In some examples, the first region 510 of the growth curve 500 may be calculated where a change in amplitude is defined in part by a residual artifact to calculate the ECAP characteristic value. In some examples, the first region 510 may be the curve below 15 mA of current. In some examples, which may depend on the method used to determine the ECAP characteristic value, a non-physiologic component of the response may manifest occasionally below the estimated neural threshold. The response grows linearly with increasing current and may be related to the residual artifact. In a second region 530 of the growth curve 500, a change in amplitude is defined in part by patient neural response. In one or more examples, near the estimated neural threshold there may be a substantial curvilinear component. In some examples, determining the estimated neural threshold is determined at least in part on a curvature of an inflection region of the growth curve 500, for example at 502. The discomfort threshold may be represented by point 504 which represents the maximum amplitude that is perceived as comfortable by the patient (e.g., amplitudes greater than point 504 are uncomfortable). In some examples, the second region 530 may be characterized by threshold ($I_{ihr}$) and sigma (how fast response grows in this region). In one or more examples, a width of the curve relates to a therapeutic range of parameter settings offered to the patient and/or clinician.

In one or more examples, the following functional form may represent the first region 510 and the second region 530, for example both the physiologic and artifact-driven, non-physiologic contributions to the ECAP growth curve 500:

$$E(I) = R(I, I_{thr}, \sigma) \cdot S_{Resp} + I \cdot S_{art} + N$$

-continued $$R(I, I_{thr}, \sigma) = \left( \sigma \, \log \left( \exp \left( -\frac{I - I_{thr}}{\sigma} \right) + 1 \right) + (I - I_{thr}) \right)$$

In one or more examples, the estimate of neural activation, E(I), at a given stimulation current, I, may be the sum of three components. The components may include R(I, $I_{thr}$, $\sigma$)·$S_{Resp}$, which captures the contribution of a neural response to the growth curve, $S_{art}$ which describes a rate of growth of the artifact with current, and constant N which is utilized to fit residual noise. The neural contribution may be characterized by parameters $I_{thr}$, $\sigma$, and $S_{Resp}$. $I_{thr}$ represents the estimated threshold for neural activation, while $\sigma$ represents the spread, a parameter that defines how quickly the curve transitions between the curvilinear and linear region as stimulation current is increased. $S_{resp}$ describes the rate of growth of neural response in the linear region. An example of the fit along with the parameters is shown FIG. 5.

Figures 6A, 6B, 6C, 6D:
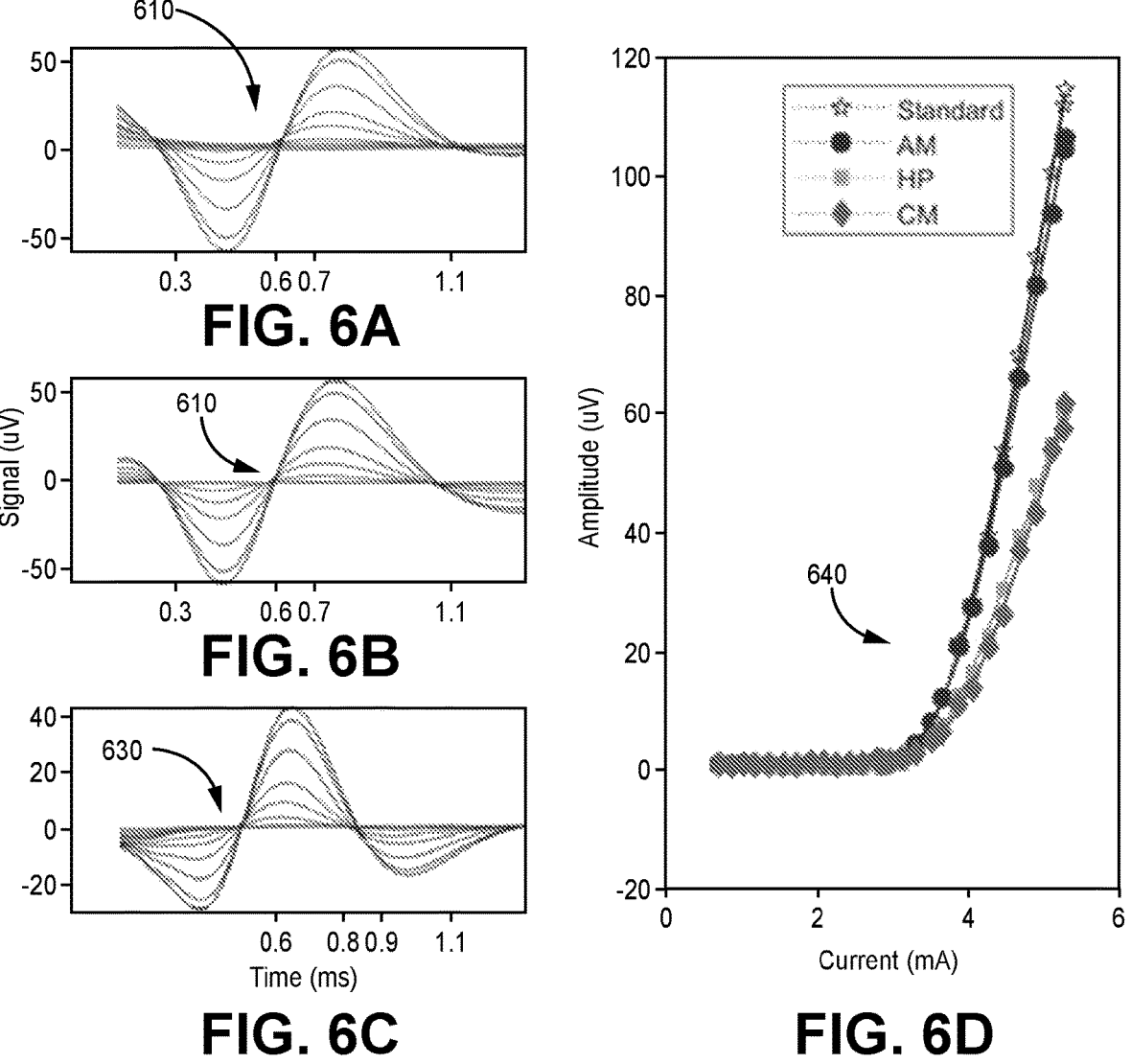
FIG. 6A is a graph of the waveforms $V_i(t)$ of an example standard method of determining ECAP characteristic values for an example response recorded from a human subject, in accordance with one or more techniques of this disclosure.
FIG. 6B is a graph of the waveforms $V_i(t)$ of an example artifact method of determining ECAP characteristic values for an example response recorded from a human subject, in accordance with one or more techniques of this disclosure.
FIG. 6C is a graph of the waveforms $V_i(t)$ of an example high-pass filter method of determining ECAP characteristic values for an example response recorded from a human subject, in accordance with one or more techniques of this disclosure.
FIG. 6D is an example growth curve of ECAP characteristic values using four different methods for determining ECAP characteristic values, in accordance with one or more techniques of this disclosure.
Figures 7A, 7B, 7C, 7D:
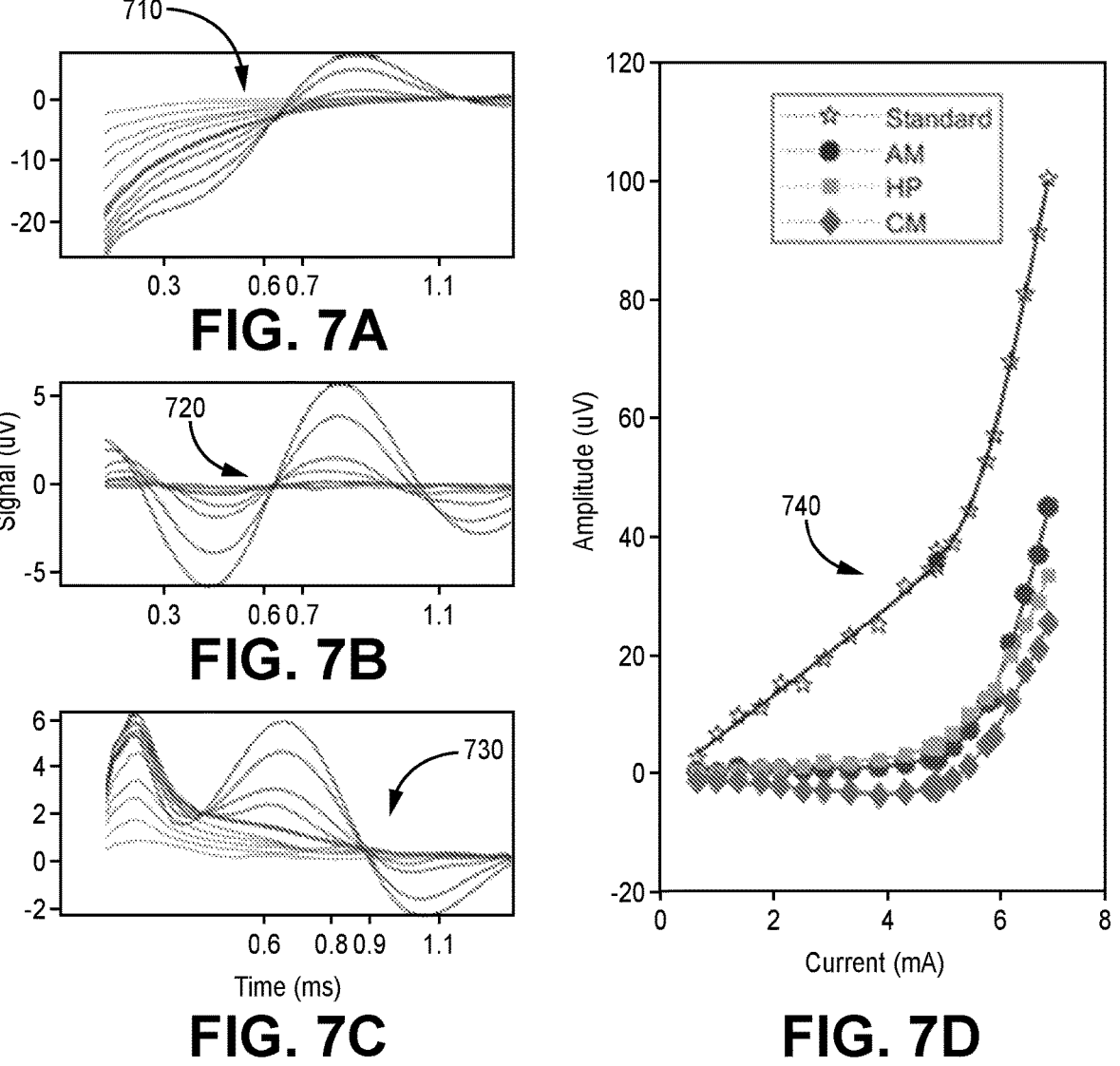
FIG. 7A is a graph of the waveforms $V_i(t)$ of an example standard method of determining ECAP characteristic values for an example response recorded from a human subject, in accordance with one or more techniques of this disclosure.
FIG. 7B is a graph of the waveforms $V_i(t)$ of an example artifact method of determining ECAP characteristic values for an example response recorded from a human subject, in accordance with one or more techniques of this disclosure.
FIG. 7C is a graph of the waveforms $V_i(t)$ of an example high-pass filter method of determining ECAP characteristic values for an example response recorded from a human subject, in accordance with one or more techniques of this disclosure.
FIG. 7D is an example growth curve of ECAP characteristic values using four different methods for determining ECAP characteristic values, in accordance with one or more techniques of this disclosure.
Figures 8A, 8B, 8C, 8D:
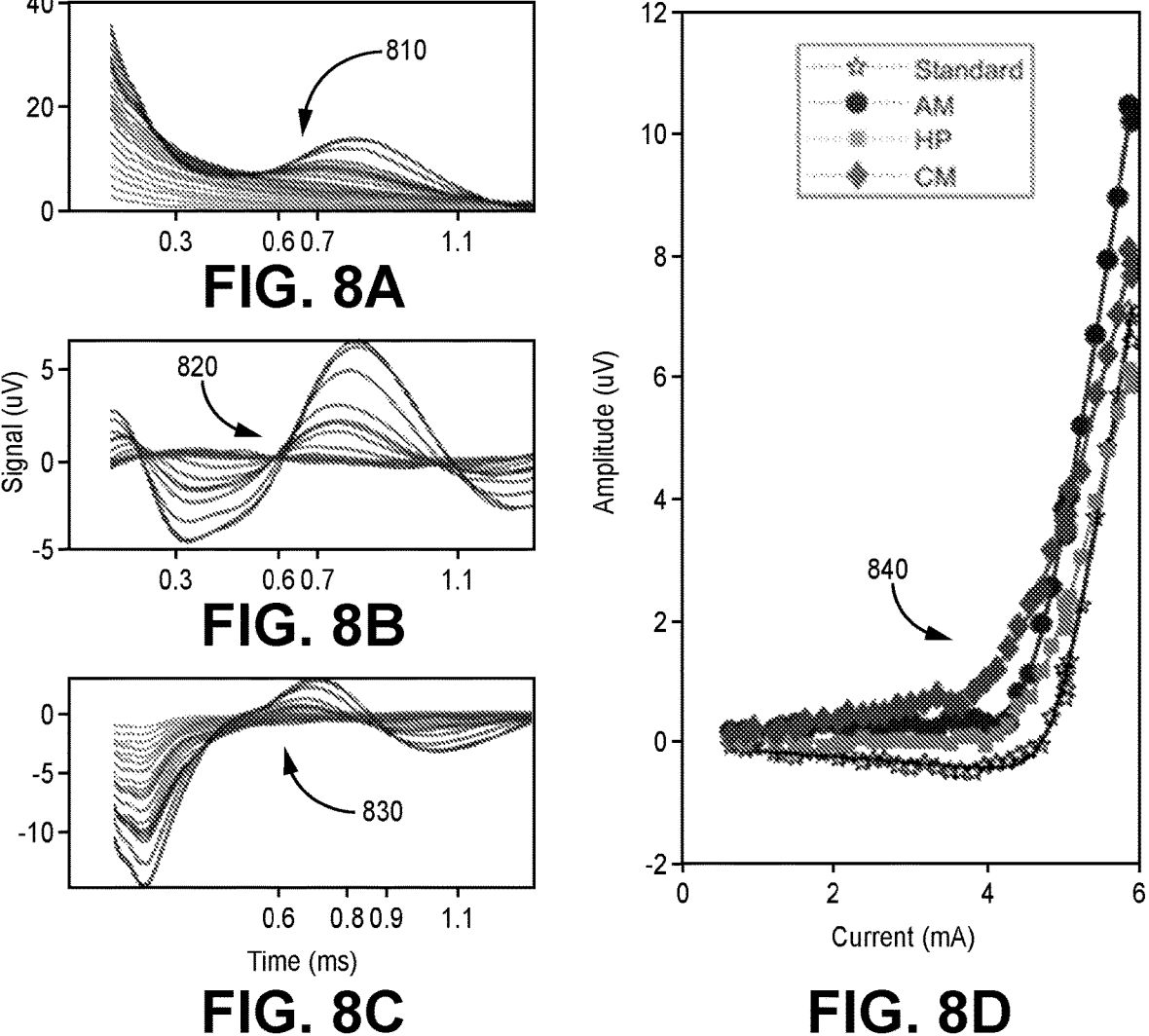
FIG. 8A is a graph of the waveforms $V_i(t)$ of an example standard method of determining ECAP characteristic values for an example response recorded from a human subject, in accordance with one or more techniques of this disclosure.
FIG. 8B is a graph of the waveforms $V_i(t)$ of an example artifact method of determining ECAP characteristic values for an example response recorded from a human subject, in accordance with one or more techniques of this disclosure.
FIG. 8C is a graph of the waveforms $V_i(t)$ of an example high-pass filter method of determining ECAP characteristic values for an example response recorded from a human subject, in accordance with one or more techniques of this disclosure.
FIG. 8D is an example growth curve of ECAP characteristic values using four different methods for determining ECAP characteristic values, in accordance with one or more techniques of this disclosure.

FIGS. 6A-D through 8A-D show three example responses recorded from a human subject that capture the types of the interaction between artifact for the ECAP signal and response encountered. For each figure, FIGS. 6A, 7A, 8A shows the waveforms $V_i(t)$ 610, 710, 810, respectively. FIGS. 6B, 7B, and 8B show outputs 620, 720, 820, respectively, of the AM methods of determining ECAP characteristic values. FIGS. 6C, 7C, and 8C show outputs 630, 730, 830, respectively, of the HP methods of determining ECAP characteristic values. FIGS. 6D, 7D, 8D show the resulting growth curves (symbols) 640, 740,840 together with their best fits (lines) for four exemplary techniques for calculating ECAP characteristic values, for example by processing circuitry.

In the case shown in FIG. 6A-D, the artifact is flat relative to the neural response, and the neural responses are clearly visible even in the standard method (FIG. 6A). In this case, the AM method (FIG. 6B) results in responses that are very similar to those seen in the raw traces. The HP method (FIG. 6C) shifts the dominant component of the response from N1 trough (in this case at approximately at 0.4 ms) to a positive peak at approximately 0.7 msec. Turning to the growth curves (FIG. 6D, 7D, 8D), the standard method is represented by star data points, the AM method is represented by a circle data points, HP method by square data points, and the CM by diamond datapoints. As shown in the figures, the AM produces the growth curve which is closest to the one achieved with the standard method. The growth curve with the HP and CM approaches underestimate the neural response (second region 530 of FIG. 5); however, the estimated threshold for neural activation $I_{thr}$ is similar across methods (Table 1).

In the cases shown in FIGS. 7A-D and 8A-D, the recorded traces Vi(t) contain both substantial artifact as well as characteristic neural response (FIGS. 7A, 8A). The growth curve for the standard method shows substantial growth at levels below where neural response is presumably occurring in the case where the artifact starts out negative and decays towards zero. In contrast, the growth cure becomes negative and then reverses to positive where the artifact starts out positive and decays to zero (FIG. 8D). In all cases, the AM substantially attenuates the artifact and reveals the neural response as shown in FIGS. 6B, 7B, 8B. The HP filter exhibits relatively large artifact early in the response, but the HP filter attenuates the artifact substantially later in the response (e.g., t>0.6 ms).

In one or more examples, qualitative observations discussed above may be captured qualitatively by examining the parameters of the fit for these examples; specifically, the degree of residual artifact may be captured by $S_{art}$, while the degree of preservation of the neural response may be captured by comparing to the neural growth slope parameter $S_{resp}$ (Table 1). The parameters of the fit of the growth curve may be utilized to quantify the effectiveness of these ECAP characteristic value development, for example to cancel artifact, while preserving the neural response.

In one or more examples, Table 1 shows parameters of the fit for the three examples in FIGS. 6D-8D. Of Table 1, Columns 3 and 4 shows the amount of artifact ($S_{art}$) and neural ($S_{resp}$) contribution to the ECAP characteristic value, respectively. Column 5 shows the calculated threshold of neural activation ($I_{thr}$).

TABLE 1

| Condition | Artifact Method | $S_{art}$ ($\mu$V/mA) | $S_{resp}$ ($\mu$V/mA) | $I_{thr}$ (mA) |
|---|---|---|---|---|
| FIG. 6 | Standard | −0.64 | 75.99 | 3.7 |
| | AM | 0.31 | 70.37 | 3.7 |
| | HP | −0.21 | 38.06 | 3.6 |
| | CM | 0.08 | 42.51 | 3.8 |
| FIG. 7 | Standard | 1.83 | 10.84 | 5.6 |
| | AM | 0.05 | 10.97 | 5.9 |
| | HP | 0.17 | 5.67 | 5.6 |
| | CM | −0.21 | 6.19 | 5.6 |
| FIG. 8 | Standard | −0.09 | 7.74 | 4.8 |
| | AM | 0.01 | 8.15 | 4.6 |
| | HP | −0.01 | 4.94 | 4.6 |
| | CM | 0.16 | 5.32 | 4.5 |

Figure 9:
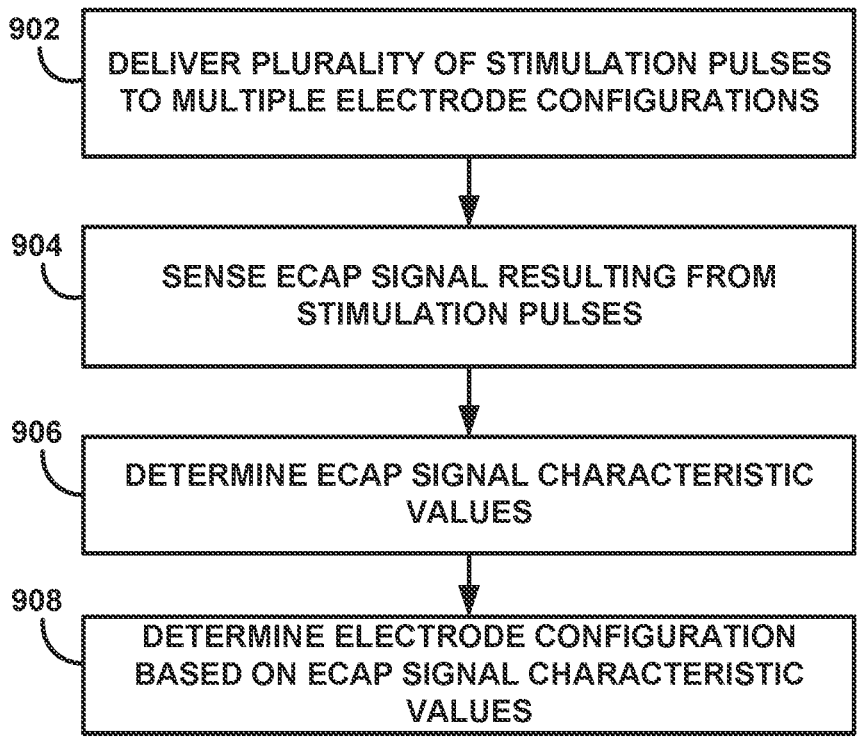
FIG. 9 is a flow diagram illustrating an example technique for determining an electrode combination and delivering electrical stimulation, in accordance with one or more techniques of this disclosure.

FIG. 9 is a flow diagram illustrating an example technique for determining an electrode combination based on ECAP signal characteristic values, in accordance with one or more techniques of this disclosure. In some examples, ECAP signal characteristic values may be a stimulation artifact. In some examples, ECAP signal characteristic values may be an electrophysiologic component. In some examples, ECAP signal characteristic values may be a stimulation artifact and an electrophysiologic component. IMD 200 and processing circuitry 210 will be described in the example of FIG. 9, but other IMDs such as IMD 110 or other devices (e.g., external programmer 150) or systems may perform, or partially perform, the technique of FIG. 9.

In one or more examples, processing circuitry 210 controls IMD 200 to deliver a plurality of stimulation pulses to multiple electrode combinations (902). In some examples, each stimulation pulse of the plurality of stimulation pulses are at least partially defined by a different respective value of a stimulation parameter, such as two or more different electrode combinations (see FIGS. 3A, 3B). In this manner, the different values of the stimulation parameter may be a testing of different electrode combinations. In some examples, the method includes selecting a candidate set of recording electrode combinations. In one or more examples, the candidate set of recording electrode combinations may include all or a subset of potential bipolar, tripolar, or multipolar combinations. In some examples, the candidate set of recording electrode combinations does not include the electrode combination used for stimulation. The processing circuitry 210 may control stimulation to iterate through the recording electrode combinations until, for example, a threshold is satisfied (e.g., exceeded or met). The processing circuitry 210 may also control IMD 200 to sense the respective ECAP signals resulting from the stimulation pulses (904) at the respective sensing electrode combinations. For example, signals are sensed for each different electrode combination. The technique includes sensing signals which may include an ECAP signal information. In some examples, the ECAP signal may include at least one of a stimulation artifact or an electrophysiologic component. In some examples, the ECAP signal may include at least one of a stimulation artifact and an electrophysiologic component.

Processing circuitry 210 uses the sensed ECAP signal information to determine ECAP characteristic values for each electrode combination (906) which, in some examples, may be based on aspects of ECAP signal information and stimulation artifact. In some examples, determining ECAP characteristic values for each electrode combination may be based on aspects of ECAP signal information or stimulation artifact.

Processing circuitry determines, based on the ECAP signal information, ECAP characteristic values for each of the ECAP signals elicited by the plurality of stimulation pulses. In some examples, the ECAP characteristic value may comprise a direct measurement, by processing circuitry, between an N1 peak and a P2 peak of the ECAP signal information. In some examples, the ECAP characteristic values may comprise the ECAP signal information with an artifact removed therefrom. In some examples, the ECAP characteristic values may be ECAP signal information with the lowest artifact or an artifact lower than artifacts present in ECAP signals from other electrode combinations. In one or more examples, removing the artifact may include modeling, for example by the processing circuitry, the artifact as a sum of a single exponential component plus a linear component, and removing the sum from each ECAP signal. In yet another example, the artifact may be sufficiently modeled solely as a linear component or exponential. In some examples, modeling the artifact by the processing circuitry includes estimating a minimum of an error function by weighting the error function higher in a first region than in a second region, where the first region is prior to a patient neural response and the second region is after the patient neural response. In one or more examples, removing the artifact comprises passing, for example by processing circuitry, the ECAP signal through a high-pass filter to determine a neural activation.

In some examples the technique includes selecting, by the processing circuitry and based on the ECAP signal information, one electrode combination from the multiple different sensing electrode combinations by comparing values for each electrode combination. In some examples, aspects of the ECAP signals and/or ECAP characteristic values are recorded for each electrode combination. The processing circuitry may determine a preferred electrode combination based on the recorded ECAP signal or the ECAP signal characteristic values or aspects of the ECAP signal or ECAP signal characteristic values (908). For example, the processing circuitry may select an electrode combination which results in an ECAP signal having an aspect of a stimulation artifact that is under a threshold. In some examples, the processing circuitry may select an electrode combination which results in an ECAP signal which has a maximum neural activation from the set of electrodes to which stimulation is applied and from which the ECAP signal is sensed. In some examples, the processing circuitry may determine a preferred electrode combination by comparing an amplitude of the artifact for the different electrode combinations. In some examples, selecting the one electrode combination includes comparing the stimulation artifacts from the respective ECAP signals from each sensing electrode combination of the different sensing electrode combinations, and determining one electrode combination as the sensing electrode combination of the different sensing electrode combinations having the lowest amplitude of the stimulation artifact. In one or more examples, the method includes selecting the one electrode combination includes comparing the electrophysiologic component from the respective ECAP signals from each sensing electrode combination of the different sensing electrode combinations, and determining the one electrode combination as the sensing electrode combination of the different sensing electrode combinations having the largest electrophysiologic component. In some examples, the aspect of the stimulation artifact may include amplitude of one or more peaks, amplitude between peaks, differences between ECAP peaks, or area under a curve. The processor may recommend or automatically implement an electrode combination that results in a lower or lowest amplitude of the stimulation artifact and/or higher or highest amplitude of the neural activation from the measured samples for the electrode combinations. In some examples, the processor may present recommended sensing configurations for confirmation by user input. In some examples, the processor may present electrode combinations and their corresponding artifact and/or ECAP values for selection by the user.

Figure 10:
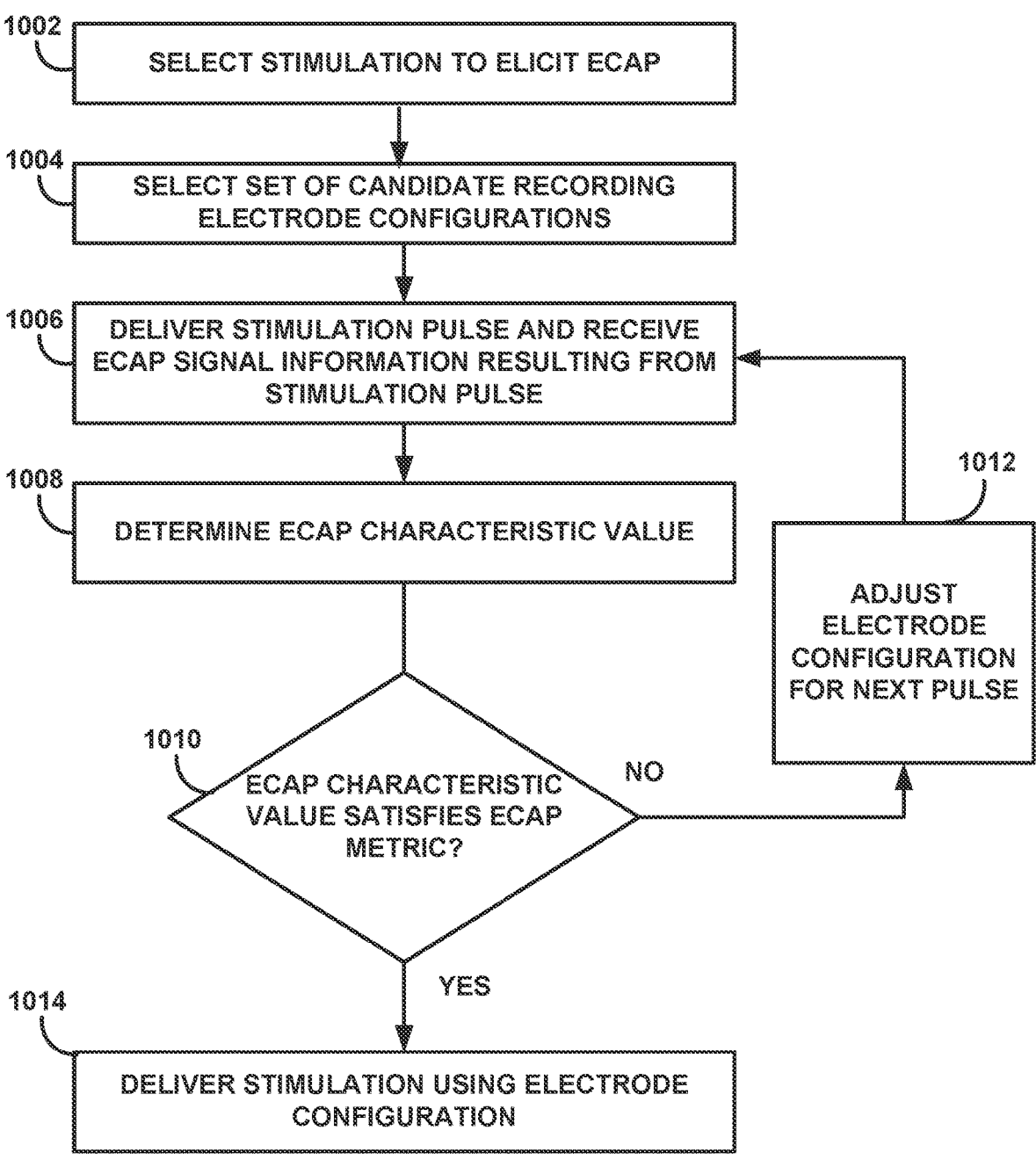
FIG. 10 is a flow chart illustrating an example technique for determining an electrode combination, in accordance with one or more techniques of this disclosure.

FIG. 10 is a flow diagram illustrating the example technique for selecting an electrode combination in accordance with one or more techniques of this disclosure. For convenience, FIG. 10 is described with respect to IMD 200 of FIG. 2. However, the techniques of FIG. 10 may be performed by different components of IMD 200 or by additional or alternative medical devices. The technique of FIG. 10 is an example feedback mechanism for controlling stimulation therapy using sensed ECAP signals.

As illustrated in FIG. 10, processing circuitry 210 of IMD 200, or via an external programmer, selects stimulation parameters desired to elicit an ECAP signal (1002), and selects a candidate set of recording electrode combinations (1004). In some examples, a candidate set of recording electrode combinations includes all or a subset of all potential bipolar, tripolar, or multipolar combinations, which may or may not be used for stimulation purposes.

Processing circuitry 210 of IMD 200 delivers a stimulation pulse to one of the candidate recording electrode combinations and senses the resulting ECAP signal elicited by the stimulation pulse (1006). Processing circuitry 210 may receive and analyze the ECAP signal to determine an ECAP characteristic value (1008), which may include the artifact, ECAP, or a combination. For example, processing circuitry 210 may determine an amplitude of an associated artifact or a neural activation for the ECAP signal.

The processing circuitry 210 evaluates whether the ECAP characteristic value has satisfied an ECAP metric (1010). In some examples, the ECAP metric is whether an amplitude of the artifact is less than a predetermined threshold. In one or more examples, the ECAP metric is whether sensitivity to neural activation exceeds a threshold. In one or more examples, the ECAP metric is whether an amplitude of a stimulation artifact is less than a predetermined threshold and/or whether sensitivity to neural activation exceeds a threshold. In one or more examples, the ECAP metric may be, the minimum stimulation artifact achieved for a plurality of electrode combinations. In one or more examples, the ECAP metric may be a maximal neural activation achieved for the plurality of electrode combinations.

If processing circuitry 210 determines that the ECAP metric has been satisfied ("YES" branch of block 1010), processing circuitry 210 moves to block 1014 and delivers stimulation at the electrode combination which satisfied the ECAP metric. If processing circuitry 210 determines that the representative characteristic value does not satisfy the ECAP metric, ("NO" branch of block 1010), processing circuitry 210 moves to block 1012.

At block 1012, processing circuitry 210 adjusts the electrode combination for the next pulse. Stimulation is delivered to elicit an ECAP signal, and the processing circuitry 210 receives ECAP signal information resulting from the stimulation pulse using the adjusted electrode combination, where the adjusted electrode combination is different than the previous electrode combination. In some examples, other stimulation parameters may be modified, such as increased or decreased amplitudes. The ECAP characteristic values may be further evaluated to determine if the value satisfies an ECAP metric, as discussed above. The ECAP characteristic values may be evaluated until an entire predetermined set or subset of electrode combinations have been tested.

Although the process of FIG. 10 is described for adjusting the electrode combinations, other stimulation parameter values may be changed in addition to the electrode combinations in other examples. For example, amplitude of the stimulation pulses (e.g., control pulses and/or stimulation pulses) may be changed. In other examples, sensed ECAP signals may be used to increase or decrease the pulse width of the stimulation pulse to adjust the amount of charge delivered to the tissue to maintain consistent volume of neural activation. In other examples, electrode combinations may be adjusted in order to deliver different amounts of charge and modify the number of neurons being recruited by each stimulation pulse. In other examples, processing circuitry 210 may be configured to adjust the pulse rate or duty cycle of the stimulation pulses.

The following are examples described herein.

Example 1. A system comprising: processing circuitry configured to: control delivery of a plurality of stimulation pulses via at least one stimulation electrode combination; receive evoked compound action potential (ECAP) signal information representing different ECAP signals evoked from respective stimulation pulses of the plurality of stimulation pulses and obtained from respective different sensing electrode combinations; and select, based on the ECAP signal information, one electrode combination from the different sensing electrode combinations.

Example 2. The system of example 1, wherein the ECAP signal information includes at least one of a stimulation artifact or an electrophysiologic component.

Example 3. The system of example 2, wherein the processing circuitry is configured to select the one electrode combination by at least determining that at least one of the stimulation artifact or the electrophysiologic component of the ECAP signal sensed obtained by the one electrode combination satisfies a threshold.

Example 4. The system of example 2, wherein the processing circuitry is configured to select the one electrode combination by at least: comparing the electrophysiologic component from the respective ECAP signals from each sensing electrode combination of the different sensing electrode combinations; and determining the one electrode combination as the sensing electrode combination of the different sensing electrode combinations having the largest electrophysiologic component.

Example 5. The system of any of examples 1 through 3, wherein the ECAP signal information comprises ECAP signals sensed by sensing circuitry and elicited by the plurality of stimulation pulses to the different electrode combinations, and wherein the processing circuitry is further configured to determine, based on the ECAP signal information, ECAP characteristic values for the ECAP signals elicited by the plurality of stimulation pulses.

Example 6. The system of example 5, wherein the processing circuitry is configured to select the one electrode combination by at least selecting, based on the ECAP characteristic values, the one electrode combination from the different electrode combinations.

Example 7. The system of any of examples 5 or 6, wherein the processing circuitry is configured to select the one electrode combination by at least selecting the one electrode combination in response to the ECAP characteristic value satisfying a threshold.

Example 8. The system of any of examples 1 through 7, wherein the plurality electrode combinations comprises different electrode combinations from an electrode array having more than eight electrodes.

Example 9. The system of any of examples 1 through 8, wherein the at least one stimulation electrode combination comprises at least one of a bipolar, a tripolar, or a multipolar electrode configuration.

Example 10. The system of any of examples 1 through 9, wherein the at least one stimulation electrode combination is different from the different sensing electrode combinations.

Example 11. The system of any of examples 1 through 10, wherein the processing circuitry is configured to: compare amplitudes of stimulation artifacts from the respective different ECAP signals from each sensing electrode combination of the different sensing electrode combinations; and determine, based on the comparison, the one electrode combination from the different sensing electrode combinations having a lowest amplitude of the stimulation artifacts, wherein the processing circuitry is configured to select the one electrode combination by at least selecting the one electrode combination having the lowest amplitude of the stimulation artifact.

Example 12. The system of any of examples 1 through 11, further comprising an implantable medical device comprising the processing circuitry.

Example 13. The system of any of examples 1 through 11, further comprising an external programmer comprising the processing circuitry, the external programmer configured to communicate with an implantable medical device configured to deliver the plurality of stimulation pulses.

Example 14. A method comprising: controlling, by processing circuitry, delivery of a plurality of stimulation pulses via at least one stimulation electrode combination; receiving, by the processing circuitry, evoked compound action potential (ECAP) signal information representing different ECAP signals evoked from respective stimulation pulses of the plurality of stimulation pulses and obtained from respective different sensing electrode combinations; and selecting, by the processing circuitry and based on the ECAP signal information, one electrode combination from the different sensing electrode combinations.

Example 15. The method of example 14, wherein the ECAP signal information includes at least one of a stimulation artifact or an electrophysiologic component.

Example 16. The method of example 15, wherein selecting the one electrode combination comprises: determining that at least one of the stimulation artifact or the electrophysiologic component of the ECAP signal sensed obtained by the one electrode combination satisfies a threshold.

Example 17. The method of example 15, wherein selecting the one electrode combination comprises: comparing the electrophysiologic component from the respective ECAP signals from each sensing electrode combination of the different sensing electrode combinations; and determining the one electrode combination as the sensing electrode combination of the different sensing electrode combinations having the largest electrophysiologic component.

Example 18. The method of any of examples 14 through 17, wherein the ECAP signal information comprises ECAP signals sensed by sensing circuitry and elicited by the plurality of stimulation pulses to the multiple different electrode combinations, further comprising determining, by the processing circuitry and based on the ECAP signal information, ECAP characteristic values for the ECAP signals elicited by the plurality of stimulation pulses.

Example 19. The method of example 18, wherein selecting, by the processing circuitry and based on the ECAP signal information comprises selecting the one electrode combination from the different electrode combinations based on ECAP characteristic values.

Example 20. The method of any of examples 18 or 19, wherein selecting the one electrode combination comprises selecting the one electrode combination in response to the ECAP characteristic value satisfying a threshold.

Example 21. The method of any of examples 14 through 20, wherein the plurality of electrode combinations comprises different electrode combinations from an electrode array having more than eight electrodes.

Example 22. The method of any of examples 14 through 21, wherein the at least one stimulation electrode combination comprises at least one of a bipolar, a tripolar, or a multipolar electrode configuration.

Example 23. The method of any of examples 14 through 22, wherein the at least one stimulation electrode combination is different from the different sensing electrode combinations.

Example 24. The method of any of examples 14 through 23, further comprising: comparing amplitudes of stimulation artifacts from the respective different ECAP signals from each sensing electrode combination of the different sensing electrode combinations; and determining, based on the comparison, one electrode combination from the different sensing electrode combinations having a lowest amplitude of the stimulation artifacts, wherein selecting the one electrode combination comprises selecting the one electrode combination having the lowest amplitude of the stimulation artifact.

Example 25. A computer-readable storage medium comprising instructions that, when executed, cause processing circuitry to: control delivery of a plurality of stimulation pulses via at least one stimulation electrode combination: receive evoked compound action potential (ECAP) signal information representing different ECAP signals evoked from respective stimulation pulses of the plurality of stimulation pulses and obtained from respective different sensing electrode combinations; and select, based on the ECAP signal information, one electrode combination from the different sensing electrode combinations.

The techniques described in this disclosure may be implemented, at least in part, in hardware, software, firmware or any combination thereof. For example, various aspects of the described techniques may be implemented within one or more processors or processing circuitry, including one or more microprocessors, digital signal processors (DSPs), application specific integrated circuits (ASICs), field programmable gate arrays (FPGAs), or any other equivalent integrated or discrete logic circuitry, as well as any combinations of such components. The term "processor" or "processing circuitry" may generally refer to any of the foregoing logic circuitry, alone or in combination with other logic circuitry, or any other equivalent circuitry. A control unit including hardware may also perform one or more of the techniques of this disclosure.

Such hardware, software, and firmware may be implemented within the same device or within separate devices to support the various operations and functions described in this disclosure. For example, processing circuitry may conduct processing off-line and conduct automatic checks of patient ECAP signals and update programming from a remote location. In addition, any of the described units, circuits or components may be implemented together or separately as discrete but interoperable logic devices. Depiction of different features as circuits or units is intended to highlight different functional aspects and does not necessarily imply that such circuits or units must be realized by separate hardware or software components. Rather, functionality associated with one or more circuits or units may be performed by separate hardware or software components or integrated within common or separate hardware or software components.

The techniques described in this disclosure may also be embodied or encoded in a computer-readable medium, such as a computer-readable storage medium, containing instructions that may be described as non-transitory media. Instructions embedded or encoded in a computer-readable storage medium may cause a programmable processor, or other processor, to perform the method. e.g., when the instructions are executed. Computer readable storage media may include random access memory (RAM), ferroelectric random access memory (FRAM), read only memory (ROM), programmable read only memory (PROM), erasable programmable read only memory (EPROM), electronically erasable programmable read only memory (EEPROM), flash memory, a hard disk, a CD-ROM, a floppy disk, a cassette, magnetic media, optical media, or other computer readable media.

What is claimed is:

1. A system comprising:
processing circuitry configured to:
control delivery of a plurality of stimulation pulses via at least one stimulation electrode combination;
receive evoked compound action potential (ECAP) signal information representing different ECAP signals evoked from respective stimulation pulses of the plurality of stimulation pulses and obtained from respective different sensing electrode combinations; and
select, based on the ECAP signal information, one sensing electrode combination from the different sensing electrode combinations.

2. The system of claim 1, wherein the ECAP signal information includes at least one of a stimulation artifact or an electrophysiologic component.

3. The system of claim 2, wherein the processing circuitry is configured to select the one sensing electrode combination by at least determining that at least one of the stimulation artifact or the electrophysiologic component of the ECAP signal sensed obtained by the one sensing electrode combination satisfies a threshold.

4. The system of claim 2, wherein the processing circuitry is configured to select the one sensing electrode combination by at least:
comparing the electrophysiologic component from the respective ECAP signals from each sensing electrode combination of the different sensing electrode combinations; and determining the one sensing electrode combination as the sensing electrode combination of the different sensing electrode combinations having the largest electrophysiologic component.

5. The system of claim 1, wherein the ECAP signal information comprises ECAP signals sensed by sensing circuitry and elicited by the plurality of stimulation pulses to the different sensing electrode combinations, and wherein the processing circuitry is further configured to determine, based on the ECAP signal information, ECAP characteristic values for the ECAP signals elicited by the plurality of stimulation pulses.

6. The system of claim 5, wherein the processing circuitry is configured to select the one sensing electrode combination by at least selecting, based on the ECAP characteristic values, the one sensing electrode combination from the different sensing electrode combinations.

7. The system of claim 5, wherein the processing circuitry is configured to select the one sensing electrode combination by at least selecting the one sensing electrode combination in response to the ECAP characteristic value satisfying a threshold.

8. The system of claim 1, wherein the plurality electrode combinations comprises different sensing electrode combinations from an electrode array having more than eight electrodes.

9. The system of claim 1, wherein the at least one stimulation electrode combination comprises at least one of a bipolar, a tripolar, or a multipolar electrode configuration.

10. The system of claim 1, wherein the at least one stimulation electrode combination is different from the different sensing electrode combinations.

11. The system of claim 1, wherein the processing circuitry is configured to:
compare amplitudes of stimulation artifacts from the respective different ECAP signals from each sensing electrode combination of the different sensing electrode combinations; and
determine, based on the comparison, the one sensing electrode combination from the different sensing electrode combinations having a lowest amplitude of the stimulation artifacts, wherein the processing circuitry is configured to select the one sensing electrode combination by at least selecting the one sensing electrode combination having the lowest amplitude of the stimulation artifact.

12. The system of claim 1, further comprising an implantable medical device comprising the processing circuitry and sensing circuitry, the sensing circuitry configured to sense subsequent ECAP signals via the one sensing electrode combination.

13. The system of claim 1, further comprising an external programmer comprising the processing circuitry, the external programmer configured to communicate with an implantable medical device configured to deliver the plurality of stimulation pulses.

14. A method comprising:
controlling, by processing circuitry, delivery of a plurality of stimulation pulses via at least one stimulation electrode combination;

receiving, by the processing circuitry, evoked compound action potential (ECAP) signal information representing different ECAP signals evoked from respective stimulation pulses of the plurality of stimulation pulses and obtained from respective different sensing electrode combinations; and
selecting, by the processing circuitry and based on the ECAP signal information, one sensing electrode combination from the different sensing electrode combinations.

15. The method of claim 14, wherein the ECAP signal information includes at least one of a stimulation artifact or an electrophysiologic component.

16. The method of claim 15, wherein selecting the one sensing electrode combination comprises determining that at least one of the stimulation artifact or the electrophysiologic component of the ECAP signal sensed obtained by the one sensing electrode combination satisfies a threshold.

17. The method of claim 15, wherein selecting the one sensing electrode combination comprises: comparing the electrophysiologic component from the respective ECAP signals from each sensing electrode combination of the different sensing electrode combinations; and determining the one sensing electrode combination as the sensing electrode combination of the different sensing electrode combinations having the largest electrophysiologic component.

18. The method of claim 14, wherein the ECAP signal information comprises ECAP signals sensed by sensing circuitry and elicited by the plurality of stimulation pulses to the different sensing electrode combinations, further comprising determining, by the processing circuitry and based on the ECAP signal information, ECAP characteristic values for the ECAP signals elicited by the plurality of stimulation pulses.

19. The method of claim 14, further comprising:
comparing amplitudes of stimulation artifacts from the respective different ECAP signals from each sensing electrode combination of the different sensing electrode combinations; and
determining, based on the comparison, one sensing electrode combination from the different sensing electrode combinations having a lowest amplitude of the stimulation artifacts, wherein selecting the one sensing electrode combination comprises selecting the one sensing electrode combination having the lowest amplitude of the stimulation artifact.

20. A non-transitory computer-readable storage medium comprising instructions that, when executed, cause processing circuitry to:
control delivery of a plurality of stimulation pulses via at least one stimulation electrode combination;
receive evoked compound action potential (ECAP) signal information representing different ECAP signals evoked from respective stimulation pulses of the plurality of stimulation pulses and obtained from respective different sensing electrode combinations; and
select, based on the ECAP signal information, one sensing electrode combination from the different sensing electrode combinations.

* * * * *